United States Patent
Ishikawa et al.

(10) Patent No.: US 8,396,525 B2
(45) Date of Patent: Mar. 12, 2013

(54) REAL-TIME SIMULTANEOUS MEASUREMENT SYSTEM, REAL-TIME SIMULTANEOUS MEASUREMENT APPARATUS, REAL-TIME SIMULTANEOUS MEASUREMENT METHOD, AND STORAGE MEDIUM IN WHICH PROGRAM IS STORED

(75) Inventors: Akihiro Ishikawa, Kyoto (JP); Tatsuya Okabe, Saitama (JP); Masaaki Sato, Kyoto (JP)

(73) Assignees: Shimadzu Corporation, Kyoto (JP); Honda Motor Co., Ltd., Tokyo (JP); Advanced Telecommunications Research Institute Research Institute International, Kyoto (JP)

( * ) Notice: Subject to any disclaimer, the term of this patent is extended or adjusted under 35 U.S.C. 154(b) by 866 days.

(21) Appl. No.: 12/488,031

(22) Filed: Jun. 19, 2009

(65) Prior Publication Data

US 2009/0318785 A1 Dec. 24, 2009

(30) Foreign Application Priority Data

Jun. 23, 2008 (JP) ................................ 2008-163092

(51) Int. Cl.
*A61B 5/00* (2006.01)
*A61B 5/04* (2006.01)
(52) U.S. Cl. .......................... 600/310; 600/320; 600/544
(58) Field of Classification Search .................. 600/310, 600/320, 473, 544
See application file for complete search history.

(56) References Cited

U.S. PATENT DOCUMENTS
2007/0083097 A1* 4/2007 Fujiwara et al. .............. 600/407

FOREIGN PATENT DOCUMENTS
JP 05-261076 10/1993
JP 2003-322612 11/2003

OTHER PUBLICATIONS

"101 Chapters Regarding Reading of Brain Waves," Igaku-Shoin Ltd., May 1999, with English abstract.

\* cited by examiner

*Primary Examiner* — Clayton E Laballe
*Assistant Examiner* — Minh Phan
(74) *Attorney, Agent, or Firm* — Cermak Nakajima LLP; Tomoko Nakajima

(57) ABSTRACT

A real-time simultaneous measurement apparatus includes: a hemoglobin information-receiving portion that sequentially receives hemoglobin information, which is information relating to the amount of hemoglobin in a head portion of a test subject, from a NIRS brain-measuring apparatus that receives a synchronization signal output by a synchronization signal output apparatus and acquires the hemoglobin information when the synchronization signal has been received; a brain wave information-receiving portion that sequentially receives the brain wave information of the test subject, from an EEG brain wave-measuring apparatus that receives a synchronization signal output by the synchronization signal output apparatus and acquires the brain wave information when the synchronization signal has been received; a synchronization processing portion that performs processing that synchronizes the hemoglobin information and the brain wave information; and an output portion that outputs the synchronized hemoglobin information and brain wave information.

13 Claims, 19 Drawing Sheets

| | 1 | 2 | 3 | 4 | 5 | 6 | 7 | 8 |
|---|---|---|---|---|---|---|---|---|
| | 1 | 0 | 0 | 0 | 0 | 0 | 0 | 0 |
| | Start | End | Event | Task1 | Task2 | Task3 | Task4 | Task5 |

FIG.10

| t | 2 | 10 | 18 | 26 | 34 | 42 | ............ |
|---|---|----|----|----|----|----|---|
| Hemoglobin information | 5 | 4 | 5 | 12 | 7 | 3 | ............ |

FIG.11

| t | 2 | 4 | 6 | 8 | 10 | 12 | 14 | 16 | 18 | 20 | 22 | 24 | 26 | 28 | 30 | 32 | 34 | 36 | 38 | 40 | 42 | ... |
|---|---|---|---|---|---|---|---|---|---|---|---|---|---|---|---|---|---|---|---|---|---|---|
| Brain wave information | 8 | 6 | 7 | 6 | 6 | 7 | 6 | 7 | 6 | 9 | 11 | 14 | 11 | 8 | 10 | 9 | 12 | 10 | 11 | 10 | 11 | ... |

FIG. 12

| Time | 2 | 4 | 6 | 8 | 10 | 12 | 14 | 16 | 18 | 20 | 22 | 24 | 26 | 28 | 30 | 32 | 34 | 36 | 38 | 40 | 42 |
|---|---|---|---|---|---|---|---|---|---|---|---|---|---|---|---|---|---|---|---|---|---|
| Brain wave information | 8 | 6 | 7 | 6 | 6 | 7 | 6 | 7 | 6 | 9 | 11 | 14 | 11 | 8 | 10 | 9 | 12 | 10 | 11 | 10 | 11 |
| Hemoglobin information | 5 | 5 | 5 | 5 | 4 | 4 | 4 | 4 | 5 | 5 | 5 | 5 | 12 | 12 | 12 | 12 | 7 | 7 | 7 | 7 | 3 |

REAL-TIME SIMULTANEOUS MEASUREMENT SYSTEM, REAL-TIME SIMULTANEOUS MEASUREMENT APPARATUS, REAL-TIME SIMULTANEOUS MEASUREMENT METHOD, AND STORAGE MEDIUM IN WHICH PROGRAM IS STORED

This application claims priority under 35 U.S.C. §119 to Japanese Patent Application No. 2008-163092, filed Jun. 23, 2008, the entirety of which is incorporated by reference herein.

BACKGROUND OF THE INVENTION

1. Field of the Invention

The present invention relates to a real-time simultaneous measurement system and the like for synchronously acquiring information, such as NIRS measurement information (similar to "hemoglobin information" described below) and EEG measurement information (similar to "brain wave information" described below), and outputting the information.

2. Description of Related Art

Conventionally, there is an apparatus that measures brain activity using the NIRS (near infrared spectroscopy) method (see JP 2003-322612A (p. 1, FIG. 1, etc.), for example). Hereinafter, the NIRS method will be described.

Hemoglobin functions as a carrier of oxygen in blood. The concentration of hemoglobin contained in blood changes according to the expansion and contraction of blood vessels. Thus, it is known that the expansion and contraction of blood vessels can be detected by measuring the hemoglobin concentration.

Thus, there is a known biological measurement method that easily and non-invasively performs measurement inside a living body using light, based on the fact that the hemoglobin concentration corresponds to oxygen metabolism inside a living body. The hemoglobin concentration can be obtained by irradiating a living body with light having a wavelength from the visible light area to the near infrared light area and measuring the amount of light that passes through the living body.

Moreover, hemoglobin binds to oxygen to form oxyhemoglobin. Furthermore, hemoglobin without the bound oxygen forms deoxyhemoglobin. It is also known that oxygen is supplied to a section that is activated by a blood flow redistribution action inside the brain, and the concentration of oxyhemoglobin that has bound to oxygen increases. Thus, measurement of the oxyhemoglobin concentration can be applied to the observation of brain activity. Oxyhemoglobin and deoxyhemoglobin have different optical absorption spectra from the visible light area to the near infrared light area, and, thus, the oxyhemoglobin concentration and the deoxyhemoglobin concentration can be obtained, for example, using near infrared light.

Thus, an optical biological measurement apparatus has been developed that includes a light-transmitting probe and a light-receiving probe in order to non-invasively measure brain activity. In such an optical biological measurement apparatus, the brain is irradiated with near infrared light using a light-transmitting probe disposed on the scalp surface of a test subject, and the amount of near infrared light emitted from the brain is detected using a light-receiving probe disposed on the scalp surface. Near infrared light passes through scalp tissues and bone tissues, and is absorbed by oxyhemoglobin and deoxyhemoglobin in blood. Thus, if the light-transmitting probe and the light-receiving probe are used to obtain information on the amount of light received, the oxyhemoglobin concentration and the deoxyhemoglobin concentration in the measurement section in the brain and a time-series change for all hemoglobin concentrations calculated based on these concentrations can be obtained as measurement data. Accordingly, activation of the brain can be measured. Measurement of brain activity performed by this sort of optical biological measurement apparatus is referred to as the NIRS method.

Furthermore, conventionally, there is an apparatus that measures brain activity using the EEG (brain waves) method (see Sadao Ichijo et al., 101 *Chapters Regarding Reading of Brain Waves*, Igaku-Shoin Ltd., May, 1999, for example). Here, EEG stands for "electroencephalography", and refers to brain waves. The EEG is a method with which an electrical change inside the brain derived from brain activity can be safely detected from the outside as a potential difference on the scalp.

Furthermore, conventionally, there is a head instrument for EEG measurement at the head portion (see JP H5-261076A (p. 1, FIG. 1, etc.), for example).

However, conventionally, NIRS measurement information and EEG measurement information cannot be synchronously acquired, and the NIRS measurement information and the EEG measurement information cannot be synchronously displayed in real time. Accordingly, there is a problem in that the state of brain activity cannot be determined in real time using NIRS and EEG. More specifically, conventionally, a change in blood flow and an electrical signal derived from brain activity cannot be measured simultaneously and in real time, and the brain state cannot be sufficiently determined.

SUMMARY OF THE INVENTION

A first aspect of the present invention is directed to a real-time simultaneous measurement system, comprising a synchronization signal output apparatus, a NIRS brain-measuring apparatus, an EEG brain wave-measuring apparatus, and a real-time simultaneous measurement apparatus, wherein the synchronization signal output apparatus comprises: a synchronization signal output portion that outputs a synchronization signal, which is a signal for synchronizing acquisition of information in the NIRS brain-measuring apparatus and the EEG brain wave-measuring apparatus, to the NIRS brain-measuring apparatus and the EEG brain wave-measuring apparatus; the NIRS brain-measuring apparatus comprises: a NIRS synchronization signal-receiving portion that receives the synchronization signal from the synchronization signal output apparatus; a hemoglobin information-acquiring portion that acquires hemoglobin information, which is information relating to an amount of hemoglobin in a head portion of a test subject, when the synchronization signal has been received by the NIRS synchronization signal-receiving portion; and a hemoglobin information-transmitting portion that sequentially transmits the hemoglobin information to the real-time simultaneous measurement apparatus; the EEG brain wave-measuring apparatus comprises: a brain wave synchronization signal-receiving portion that receives the synchronization signal from the synchronization signal output apparatus; a brain wave information-acquiring portion that acquires brain wave information, which is information relating to brain waves of the test subject, when the synchronization signal has been received by the brain wave synchronization signal-receiving portion; and a brain wave information-transmitting portion that sequentially transmits the brain wave information to the real-time simultaneous measurement apparatus; and the real-time simultaneous measurement apparatus comprises: a hemoglobin information-receiving portion that sequentially receives the hemoglobin information; a brain wave information-receiving portion that sequentially receives the brain wave information; a synchronization processing portion that performs processing that synchronizes the hemoglobin information and the brain wave information; and an output portion that outputs the synchronized hemoglobin information and brain wave information.

With this configuration, the NIRS measurement information and the EEG measurement information can be precisely synchronized, and the brain state can be determined while the NIRS measurement information and the EEG measurement information are displayed in real time. Furthermore, the relationship between a change in the blood flow of the brain that can be measured by NIRS, the electrical activity of the brain that can be measured by EEG, and the like can be clarified. Here, in this real-time simultaneous measurement system, the synchronization signal output apparatus is used to synchronize the NIRS measurement information and the EEG measurement information, and, thus, both types of information can be very precisely synchronized.

Furthermore, a second aspect of the present invention is directed to the real-time simultaneous measurement system according to the first aspect, wherein the synchronization signal output portion of the synchronization signal output apparatus comprises: a first synchronization signal output unit that outputs a synchronization signal realized by an electrical signal to the NIRS brain-measuring apparatus and the EEG brain wave-measuring apparatus; a second synchronization signal output unit that outputs a synchronization signal realized using software to the NIRS brain-measuring apparatus and the EEG brain wave-measuring apparatus; a selection information storage unit in which selection information indicating which synchronization signal output unit, of the first and second synchronization signal output units, outputs a synchronization signal is stored; and a synchronization signal output-instructing unit that gives either the first synchronization signal output unit or the second synchronization signal output unit an instruction to output a synchronization signal, according to the selection information.

With this configuration, a communication unit that matches the specification of peripheral apparatuses can be selected and used. Furthermore, two types of communication units can be switched so that the NIRS measurement information and the EEG measurement information can be acquired while using the best properties of each communication unit.

Furthermore, a third aspect of the present invention is directed to the real-time simultaneous measurement system according to either the first or the second aspect, wherein the real-time simultaneous measurement apparatus further comprises: a first shared memory in which the hemoglobin information can be stored; and a second shared memory in which the brain wave information can be stored; and the synchronization processing portion comprises: a hemoglobin information storing unit that writes the hemoglobin information to the first shared memory; a brain wave information storing unit that writes the brain wave information to the second shared memory; and a synchronization processing unit that reads the hemoglobin information from the first shared memory and the brain wave information from the second shared memory and performs processing that synchronizes the hemoglobin information and the brain wave information.

With this configuration, not only simultaneous measurement of NIRS and EEG but also measurement of only NIRS or measurement of only EEG can be performed in real time using the same system, without changing the system at all.

Furthermore, a fourth aspect of the present invention is directed to the real-time simultaneous measurement system according to either the first or the second aspect, further comprising a first operating apparatus, a second operating apparatus, and a third operating apparatus, wherein the first operating apparatus comprises: an instruction-accepting portion that accepts an instruction from a user; and an instruction-transmitting portion that transmits the instruction to the first operating apparatus and the second operating apparatus; the second operating apparatus comprises: a second instruction-receiving portion that receives the instruction from the first operating apparatus; and a second instruction-transmitting portion that transmits the instruction received by the second instruction-receiving portion to the NIRS brain-measuring apparatus; and the third operating apparatus comprises: a third instruction-receiving portion that receives the instruction from the first operating apparatus; and a third instruction-transmitting portion that transmits the instruction received by the third instruction-receiving portion to the EEG brain wave-measuring apparatus.

With this configuration, the same instruction can be simultaneously given to the NIRS brain-measuring apparatus and the EEG brain wave-measuring apparatus, and, thus, both the NIRS brain-measuring apparatus and the EEG brain wave-measuring apparatus can be controlled by the first operating apparatus.

Furthermore, a fifth aspect of the present invention is directed to the real-time simultaneous measurement system according to any one of the first to the fourth aspects, wherein the real-time simultaneous measurement apparatus further comprises: an information storage portion in which information can be stored; and an information output portion that outputs the information; and the output portion accumulates the synchronized hemoglobin information and brain wave information, and the information output by the information output portion in association with each other.

With this configuration, the influence of the information output to the test subject on the brain state can be analyzed in real time and more accurately.

Furthermore, a sixth aspect of the present invention is directed to the real-time simultaneous measurement system according to any one of the first to the fifth aspects, wherein a first sampling frequency at which the hemoglobin information-acquiring portion acquires the hemoglobin information and a second sampling frequency at which the brain wave information-acquiring portion acquires the brain wave information differ, and the synchronization processing portion synchronizes the hemoglobin information and the brain wave information by acquiring hemoglobin information or brain wave information corresponding to the larger sampling frequency, of the first sampling frequency and the second sampling frequency, and subjecting brain wave information or hemoglobin information corresponding to the smaller sampling frequency to processing that copies information received at the closest time point or processing that extrapolates or interpolates received information so that the number of pieces of information is the same as that of the larger sampling frequency.

With this configuration, brain state can be precisely determined by solving the differences in the results for the different specifications of the NIRS brain-measuring apparatus and the EEG brain wave-measuring apparatus.

Furthermore, a seventh aspect of the present invention is directed to the real-time simultaneous measurement system according to any one of the first to the sixth aspects, wherein the real-time simultaneous measurement system further comprises a biological information-acquiring apparatus, the biological information-acquiring apparatus comprises: a biological information-acquiring portion that sequentially acquires biological information, which is information relating to a living body, from at least one section of the test subject; and a biological information-transmitting portion that sequentially transmits the biological information to the real-time simultaneous measurement apparatus; the real-time simultaneous measurement apparatus further comprises a biological information-receiving portion that sequentially receives the biological information, the synchronization processing portion of the real-time simultaneous measurement apparatus performs processing that synchronizes the hemoglobin information, the brain wave information, and the biological information, and the output portion outputs the synchronized hemoglobin information, brain wave information, and biological information.

With this configuration, the biological information obtained during the measurement of brain activity also can be used, and, thus, the brain state can be more precisely determined. For example, an artifact using biological information, such as electromyography information, electrooculography information, or electrocardiography information, can be preferably removed.

Furthermore, an eighth aspect of the present invention is directed to the real-time simultaneous measurement system according to the seventh aspect, wherein the biological information-acquiring portion sequentially acquires electromyography information, which is information relating to electromyography, from the whole or part of the body of the test subject, electrooculography information, which is information relating to electrooculography, from sections surrounding the eyes of the test subject, or electrocardiography information, which is information relating to electrocardiography, from sections surrounding the heart of the test subject.

With this configuration, an artifact such as biological information that causes noise during measurement of the brain activity (e.g., the electromyography information, the electrooculography information, or the electrocardiography information) can be removed, and, thus, the brain state can be more precisely determined.

Furthermore, a ninth aspect of the present invention is directed to the real-time simultaneous measurement system according to any one of the first to the eighth aspects, wherein each of the hemoglobin information and the brain wave information, or each of hemoglobin information, brain wave information, and biological information has a synchronization signal associated therewith, the real-time simultaneous measurement apparatus receives the hemoglobin information associated with the synchronization signal and the brain wave information associated with the synchronization signal, or the hemoglobin information associated with the synchronization signal, the brain wave information associated with the synchronization signal, and the biological information associated with the synchronization signal at different timings, and the synchronization processing portion receives the hemoglobin information associated with the synchronization signal and the brain wave information associated with the synchronization signal, or the hemoglobin information associated with the synchronization signal, the brain wave information associated with the synchronization signal, and the biological information associated with the synchronization signal, and then performs processing that synchronizes the hemoglobin information and the brain wave information, or the hemoglobin information, the brain wave information, and the biological information.

With this configuration, for example, even in a state where the NIRS brain-measuring apparatus and the EEG brain wave-measuring apparatus respectively measure the hemoglobin information and the brain wave information at different timings, both types of information can be synchronized later.

Furthermore, a tenth aspect of the present invention is directed to the real-time simultaneous measurement system according to any one of the first to the eighth aspects, comprising a synchronization signal output apparatus, a NIRS brain-measuring apparatus, an EEG brain wave-measuring apparatus, and multiple real-time simultaneous measurement apparatuses, or comprising a synchronization signal output apparatus, a NIRS brain-measuring apparatus, an EEG brain wave-measuring apparatus, a biological information-acquiring apparatus, and multiple real-time simultaneous measurement apparatuses, wherein the hemoglobin information-transmitting portion and the brain wave information-transmitting portion, or the hemoglobin information-transmitting portion, the brain wave information-transmitting portion, and the biological information-transmitting portion respectively transmit the hemoglobin information and the brain wave information, or the hemoglobin information, the brain wave information, and the biological information to the multiple real-time simultaneous measurement apparatuses.

With this configuration, in a case where applications that operate on the multiple real-time simultaneous measurement apparatuses use the hemoglobin information, the brain wave information, and the biological information, they need only access their own shared memory, and delays in accessing a shared memory can be solved.

With the real-time simultaneous measurement system according to the present invention, the NIRS measurement information and the EEG measurement information can be precisely synchronized.

BRIEF DESCRIPTION OF THE DRAWINGS

FIG. 10 is a diagram showing an example of information transmitted to a NIRS brain-measuring apparatus and the like in this embodiment.

FIG. 11 is a diagram showing hemoglobin information received by the real-time simultaneous measurement apparatus in this embodiment.

FIG. 12 is a diagram showing brain wave information received by the real-time simultaneous measurement apparatus in this embodiment.

FIG. 15 is a diagram showing information after synchronization processing in this embodiment.

DETAILED DESCRIPTION OF THE INVENTION

Figure 1:
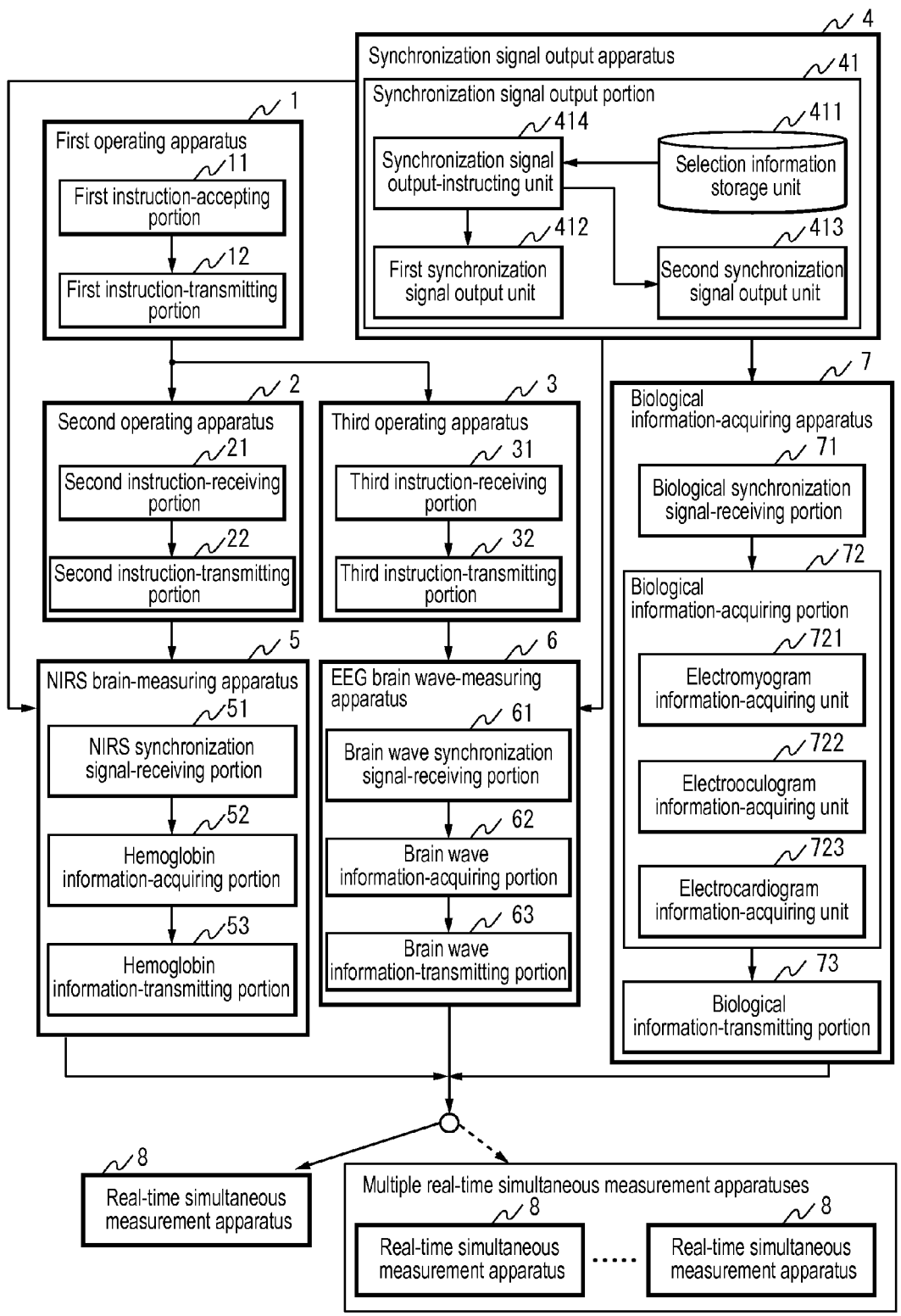
FIG. 1 is a block diagram of a real-time simultaneous measurement system in an embodiment.

Hereinafter, embodiments of a real-time simultaneous measurement system and the like will be described with reference to the drawings. It should be noted that constituent elements denoted by the same reference numerals in the embodiments perform similar operations, and, thus, a description thereof may not be repeated.

Embodiment

In this embodiment, a real-time simultaneous measurement system that synchronously acquires and outputs NIRS measurement information and EEG measurement information will be described. This real-time simultaneous measurement system includes an apparatus for synchronization (a synchronization signal output apparatus 4 described below). Furthermore, in this embodiment, a real-time simultaneous measurement system that synchronously acquires and outputs NIRS measurement information, EEG measurement information, and biological information will be described.

FIG. 1 is a block diagram of a real-time simultaneous measurement system in this embodiment. The real-time simultaneous measurement system includes a first operating apparatus 1, a second operating apparatus 2, a third operating apparatus 3, a synchronization signal output apparatus 4, a NIRS brain-measuring apparatus 5, an EEG brain wave-measuring apparatus 6, a biological information-acquiring apparatus 7, and a real-time simultaneous measurement apparatus 8. The real-time simultaneous measurement system may include multiple real-time simultaneous measurement apparatuses 8.

The first operating apparatus 1 includes a first instruction-accepting portion 11 and a first instruction-transmitting portion 12. The second operating apparatus 2 includes a second instruction-receiving portion 21 and a second instruction-transmitting portion 22. The third operating apparatus 3 includes a third instruction-receiving portion 31 and a third instruction-transmitting portion 32.

The synchronization signal output apparatus 4 includes a synchronization signal output portion 41. The synchronization signal output portion 41 includes a selection information storage unit 411, a first synchronization signal output unit 412, a second synchronization signal output unit 413, and a synchronization signal output-instructing unit 414.

The NIRS brain-measuring apparatus 5 includes a NIRS synchronization signal-receiving portion 51, a hemoglobin information-acquiring portion 52, and a hemoglobin information-transmitting portion 53.

The EEG brain wave-measuring apparatus 6 includes a brain wave synchronization signal-receiving portion 61, a brain wave information-acquiring portion 62, and a brain wave information-transmitting portion 63.

The biological information-acquiring apparatus 7 includes a biological synchronization signal-receiving portion 71, a biological information-acquiring portion 72, and a biological information-transmitting portion 73. The biological information-acquiring portion 72 includes an electromyography information-acquiring unit 721, an electrooculography information-acquiring unit 722, and an electrocardiography information-acquiring unit 723.

Figure 2:
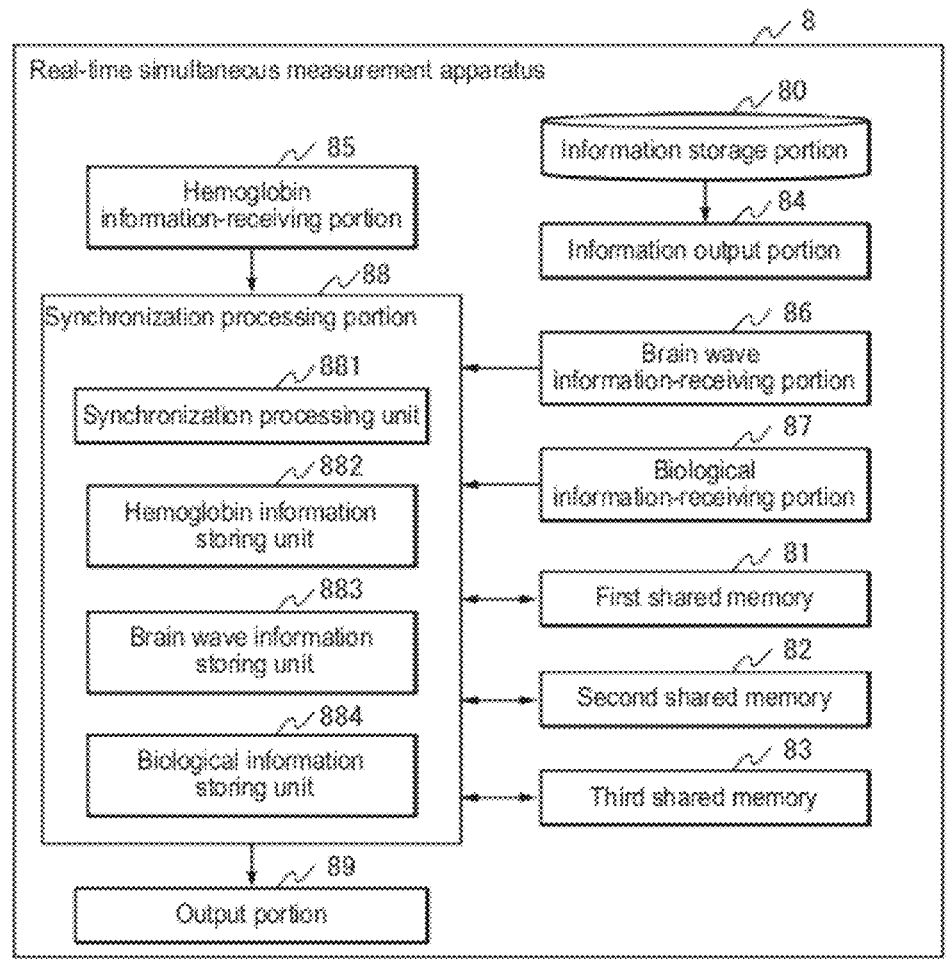
FIG. 2 is a block diagram of a real-time simultaneous measurement apparatus in this embodiment.

FIG. 2 is a block diagram of the real-time simultaneous measurement apparatus 8. The real-time simultaneous measurement apparatus 8 includes an information storage portion 80, a first shared memory 81, a second shared memory 82, a third shared memory 83, an information output portion 84, a hemoglobin information-receiving portion 85, a brain wave information-receiving portion 86, a biological information-receiving portion 87, a synchronization processing portion 88, and an output portion 89. The synchronization processing portion 88 includes a synchronization processing unit 881, a hemoglobin information storing unit 882, a brain wave information storing unit 883, and a biological information storing unit 884.

The first instruction-accepting portion 11 accepts an instruction from a user. The instruction is, for example, an instruction to operate the NIRS brain-measuring apparatus 5 and the EEG brain wave-measuring apparatus 6. Furthermore, the instruction is, for example, an instruction to start measurement in each apparatus. As an input unit of the instruction, any unit may be used such as a keyboard, a mouse, a numeric keypad, a menu screen, and the like. The first instruction-accepting portion 11 may be realized as a device driver for an input unit, such as a keyboard, or control software for a menu screen, for example.

The first instruction-transmitting portion 12 transmits an instruction accepted by the first instruction-accepting portion 11 to the second operating apparatus 2 and the third operating apparatus 3. Here, the first instruction-transmitting portion 12 may transmit the instruction to the biological information-acquiring apparatus 7, or may transmit the instruction to a fourth operating apparatus (not shown) connected to the biological information-acquiring apparatus 7. The first instruction-transmitting portion 12 is realized typically as a wireless or wired communication unit, but may be realized also as a broadcasting unit.

The second instruction-receiving portion 21 receives the instruction from the first operating apparatus 1.

The second instruction-transmitting portion 22 transmits the instruction received by the second instruction-receiving portion 21 to the NIRS brain-measuring apparatus 5. The second instruction-receiving portion 21 and the second instruction-transmitting portion 22 are realized typically as a wireless or wired communication unit, but may be realized also as a broadcasting unit.

The third instruction-receiving portion 31 receives the instruction from the first operating apparatus 1.

The third instruction-transmitting portion 32 transmits the instruction received by the third instruction-receiving portion 31 to the EEG brain wave-measuring apparatus 6. The third instruction-receiving portion 31 and the third instruction-transmitting portion 32 are realized typically as a wireless or wired communication unit, but may be realized also as a broadcasting unit.

The synchronization signal output portion 41 outputs a synchronization signal, which is a signal for synchronizing the acquisition of information in the NIRS brain-measuring apparatus 5 and the EEG brain wave-measuring apparatus 6, to the NIRS brain-measuring apparatus 5 and the EEG brain wave-measuring apparatus 6. The synchronization signal is typically regularly output, but also may be irregularly output. The synchronization signal output portion 41 typically outputs the synchronization signal using clock signals of its own clock. Here, the output is typically transmission. The synchronization signal output portion 41 is realized typically as a wireless or wired communication unit, but may be realized also as a broadcasting unit.

In the selection information storage unit 411, selection information indicating which synchronization signal output unit, of the two synchronization signal output units (the first synchronization signal output unit 412 and the second synchronization signal output unit 413), outputs a synchronization signal is stored. The selection information is, for example, either "1" (to select the first synchronization signal output unit 412) or "0" (to select the second synchronization signal output unit 413). The selection information storage unit 411 is preferably a non-volatile storage medium, but may be realized also as a volatile storage medium. There is no limitation on the procedure in which the selection information is stored in the selection information storage unit 411. For example, the selection information may be stored in the selection information storage unit 411 via a storage medium, the selection information transmitted via a communication line or the like may be stored in the selection information storage unit 411, or the selection information input via an input device may be stored in the selection information storage unit 411.

The first synchronization signal output unit 412 outputs a synchronization signal realized by an electrical signal to the NIRS brain-measuring apparatus 5 and the EEG brain wave-measuring apparatus 6. That is to say, this synchronization signal can be said to be a hardware-related signal. The first synchronization signal output unit 412 transmits the synchronization signal, for example, via a BNC cable. The first synchronization signal output unit 412 has less overhead in communications and can more accurately synchronize the acquisition of information in the NIRS brain-measuring apparatus 5, the EEG brain wave-measuring apparatus 6, and the biological information-acquiring apparatus 7, compared with the second synchronization signal output unit 413 described below. The first synchronization signal output unit 412 is realized typically as a wireless or wired communication unit, but may be realized also as a broadcasting unit.

The second synchronization signal output unit 413 outputs a synchronization signal realized using software to the NIRS brain-measuring apparatus 5 and the EEG brain wave-measuring apparatus 6. That is to say, this synchronization signal can be said to be a software-related signal. The second synchronization signal output unit 413 makes it possible to adjust surrounding facilities more easily, compared with the first synchronization signal output unit 412. The second synchronization signal output unit 413 transmits the synchronization signal, for example, via a LAN. The second synchronization signal output unit 413 is realized typically as a wireless or wired communication unit, but may be realized also as a broadcasting unit.

The synchronization signal output-instructing unit 414 gives either the first synchronization signal output unit 412 or the second synchronization signal output unit 413 an instruction to output a synchronization signal, according to the selection information stored in the selection information storage unit 411. Then, the first synchronization signal output unit 412 or the second synchronization signal output unit 413 outputs a synchronization signal according to the instruction given by the synchronization signal output-instructing unit 414. Here, the operation of giving an instruction to output a synchronization signal is, for example, processing that starts any one of the communication units, or calling a function or method corresponding to any one of the communication units. The operation need only be processing that causes, as a result, a synchronization signal to be output by any one of communication units. The synchronization signal output-instructing unit 414 may be realized typically as an MPU, a memory, or the like. Typically, the processing procedure of the synchronization signal output-instructing unit 414 is realized using software, and the software is stored in a storage medium, such as a ROM. Note that the processing procedure may be realized also using hardware (a dedicated circuit).

The NIRS brain-measuring apparatus 5 is an apparatus that non-invasively performs brain function mapping on the scalp using near infrared light, and is an apparatus that uses the principle of "NIRS-Imaging". Typically, the NIRS brain-measuring apparatus 5 accepts an instruction to start measurement, sequentially acquires hemoglobin information, and transmits the information to the real-time simultaneous measurement apparatus 8. Furthermore, the NIRS brain-measuring apparatus 5 acquires the hemoglobin information according to the synchronization signal received from the synchronization signal output apparatus 4.

The NIRS synchronization signal-receiving portion 51 receives the synchronization signal from the synchronization signal output apparatus 4. The NIRS synchronization signal-receiving portion 51 is realized typically as a wireless or wired communication unit, but may be realized also as a unit that receives a broadcast.

The hemoglobin information-acquiring portion 52 acquires hemoglobin information, which is information relating to the amount of hemoglobin in a head portion of a test subject, when the synchronization signal has been received by the NIRS synchronization signal-receiving portion 51. Here, acquisition when the synchronization signal has been received refers to acquisition of the hemoglobin information after receiving the synchronization signal in a case where the synchronization signal is regularly received. It is preferable that the hemoglobin information-acquiring portion 52 acquires the hemoglobin information when the synchronization signal has been received by the NIRS synchronization signal-receiving portion 51, and then regularly and sequentially acquires the hemoglobin information. Furthermore, the hemoglobin information-acquiring portion 52 may acquire the hemoglobin information only after the synchronization signal has been received by the NIRS synchronization signal-receiving portion 51. Typically, the hemoglobin information-acquiring portion 52 sequentially acquires hemoglobin information, which is information relating to the amount of hemoglobin in a head portion of a test subject. The hemoglobin information-acquiring portion 52 sequentially acquires the hemoglobin information at a first sampling frequency. Here, the first sampling frequency is typically different from a second sampling frequency described below. The first sampling frequency is, for example, 40 Hz. The hemoglobin information-acquiring portion 52 can be realized using a known art, and, thus, a detailed description thereof has been omitted. Furthermore, there is no limitation on the data structure of the hemoglobin information. The hemoglobin information may be the amount of hemoglobin, or may be a voltage for calculating the amount of hemoglobin, or the like. Examples of the hemoglobin information will be described below. The hemoglobin information-acquiring portion 52 may be realized typically as an MPU, a memory, or the like. Typically, the processing procedure of the hemoglobin information-acquiring portion 52 is realized using software, and the software is stored in a storage medium, such as a ROM.

Note that the processing procedure may be realized also using hardware (a dedicated circuit).

The hemoglobin information-transmitting portion 53 sequentially transmits the hemoglobin information to the real-time simultaneous measurement apparatus 8. The hemoglobin information-transmitting portion 53 may sequentially transmit the hemoglobin information to the multiple real-time simultaneous measurement apparatuses 8. In this case, the hemoglobin information-transmitting portion 53 sequentially transmits the hemoglobin information to the multiple real-time simultaneous measurement apparatuses 8, for example, by multicast. In a case where applications that operate on the multiple real-time simultaneous measurement apparatuses 8 use the hemoglobin information, they need only access their own shared memory, and delays in accessing a shared memory can be solved. The hemoglobin information-transmitting portion 53 is realized typically as a wireless or wired communication unit, but may be realized also as a broadcasting unit.

The EEG brain wave-measuring apparatus 6 is an apparatus that measures brain waves. Example of the apparatus that has a function of measuring brain waves include an apparatus (ActiveTwo system) manufactured by BioSemi. Typically, the EEG brain wave-measuring apparatus 6 accepts an instruction to start measurement, sequentially acquires brain wave information, and transmits the information to the real-time simultaneous measurement apparatus 8. Furthermore, the EEG brain wave-measuring apparatus 6 acquires the brain wave information according to the synchronization signal received from the synchronization signal output apparatus 4.

The brain wave synchronization signal-receiving portion 61 receives the synchronization signal from the synchronization signal output apparatus 4. The brain wave synchronization signal-receiving portion 61 is realized typically as a wireless or wired communication unit, but may be realized also as a unit that receives a broadcast.

The brain wave information-acquiring portion 62 acquires brain wave information, which is information relating to brain waves of the test subject, when the synchronization signal has been received by the brain wave synchronization signal-receiving portion 61. Here, acquisition when the synchronization signal has been received refers to acquisition of the brain wave information after receiving the synchronization signal in a case where the synchronization signal is regularly received. It is preferable that the brain wave information-acquiring portion 62 acquires the brain wave information when the synchronization signal has been received by the brain wave synchronization signal-receiving portion 61, and then regularly and sequentially acquires the brain wave information. Furthermore, the brain wave information-acquiring portion 62 may acquire the brain wave information only after the synchronization signal has been received by the brain wave synchronization signal-receiving portion 61. Typically, the brain wave information-acquiring portion 62 sequentially acquires brain wave information, which is information relating to brain waves of the test subject. The brain wave information-acquiring portion 62 sequentially acquires the brain wave information at a second sampling frequency. Here, the second sampling frequency is, for example, 1024 Hz. The brain wave information-acquiring portion 62 can be realized using a known art, and, thus, a detailed description thereof has been omitted. Furthermore, the brain wave information is, for example, a potential difference (the unit is, for example, a "microvolt") on the scalp. The brain wave information-acquiring portion 62 may be realized typically as an MPU, a memory, or the like. Typically, the processing procedure of the brain wave information-acquiring portion 62 is realized using software, and the software is stored in a storage medium, such as a ROM. Note that the processing procedure may be realized also using hardware (a dedicated circuit).

The brain wave information-transmitting portion 63 sequentially transmits the brain wave information acquired by the brain wave information-acquiring portion 62 to the real-time simultaneous measurement apparatus 8. The brain wave information-transmitting portion 63 may sequentially transmit the brain wave information to the multiple real-time simultaneous measurement apparatuses 8. In this case, the brain wave information-transmitting portion 63 sequentially transmits the brain wave information to the multiple real-time simultaneous measurement apparatuses 8, for example, by multicast. In a case where applications that operate on the multiple real-time simultaneous measurement apparatuses 8 use the brain wave information, they need only access their own shared memory, and delays in accessing a shared memory can be solved. The brain wave information-transmitting portion 63 is realized typically as a wireless or wired communication unit, but may be realized also as a broadcasting unit.

The biological information-acquiring apparatus 7 is an apparatus that acquires biological information. The biological information will be described below. Typically, the biological information-acquiring apparatus 7 accepts an instruction to start measurement, sequentially acquires biological information, and transmits the information to the real-time simultaneous measurement apparatus 8. Furthermore, the biological information-acquiring apparatus 7 acquires the biological information according to the synchronization signal received from the synchronization signal output apparatus 4.

The biological synchronization signal-receiving portion 71 receives the synchronization signal from the synchronization signal output apparatus 4. The biological synchronization signal-receiving portion 71 is realized typically as a wireless or wired communication unit, but may be realized also as a unit that receives a broadcast.

The biological information-acquiring portion 72 acquires the biological information in a head portion of a test subject when the synchronization signal has been received by the biological synchronization signal-receiving portion 71. Here, acquisition when the synchronization signal has been received refers to acquisition of the biological information after receiving the synchronization signal in a case where the synchronization signal is regularly received. It is preferable that the biological information-acquiring portion 72 acquires the biological information when the synchronization signal has been received by the biological synchronization signal-receiving portion 71, and then regularly and sequentially acquires the biological information. Furthermore, the biological information-acquiring portion 72 may acquire the biological information only after the synchronization signal has been received by the biological synchronization signal-receiving portion 71. Typically, the biological information-acquiring portion 72 sequentially acquires biological information, which is information relating to a living body, from one or more sections of the test subject. Here, the biological information is information containing one or more types of information among electromyography information, electrooculography information, and electrocardiography information. The electromyography information is information relating to electromyography (EMG) that can be acquired from the whole or part of the body of the test subject. The electrooculography information is information relating to electrooculography (EOG) that can be acquired from sections surrounding the eyes of the test subject. The electrocardiography information is information relating to electrocardiography (ECG) that can be acquired from sections surrounding the heart of the test subject. Furthermore, the biological information-acquiring portion 72 can be realized using a known art, and, thus, a detailed description thereof has been omitted.

The electromyography information-acquiring unit 721 sequentially acquires the electromyography information from the whole or part of the body of the test subject. It is preferable that the electromyography information-acquiring unit 721 sequentially acquires the electromyography information from four sections on the left and right arm portions of the test subject as shown in FIG. 3.

Figure 3:
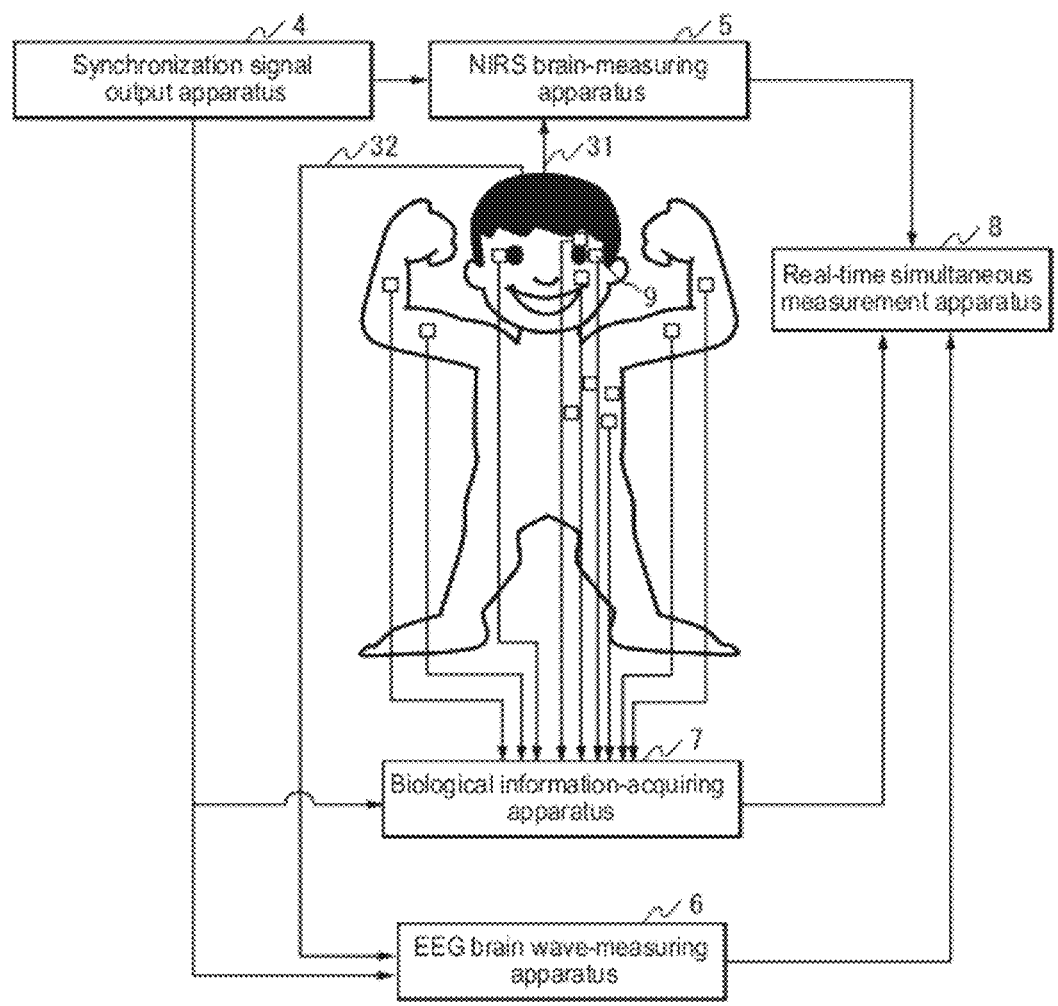
FIG. 3 is a conceptual diagram of the real-time simultaneous measurement system in this embodiment.

It is preferable that the electrooculography information-acquiring unit 722 sequentially acquires the electrooculography information from four sections on the face portion of the test subject as shown in FIG. 3.

It is preferable that the electrocardiography information-acquiring unit 723 sequentially acquires the electrocardiography information from sections surrounding the heart of the test subject as shown in FIG. 3.

Here, small rectangles (9) in FIG. 3 are electrodes for acquiring the electromyography information, the electrooculography information, or the electrocardiography information. Furthermore, in FIG. 3, the number of channels for the hemoglobin information that is acquired by the NIRS brain-measuring apparatus 5 is, for example, 48. That is to say, the number of signals that flow through Line 31 is, 48. Furthermore, the number of channels for the brain wave information that is acquired by the EEG brain wave-measuring apparatus 6 is, for example, 64. That is to say, the number of signals that flow through Line 32 is, 64. Furthermore, the electromyography information is, for example, an action potential that is generated in the excitation of muscular fibers. Furthermore, it will be appreciated that the number of channels for the hemoglobin information that is acquired by the NIRS brain-measuring apparatus 5 and the number of channels for the brain wave information that is acquired by the EEG brain wave-measuring apparatus 6 are not limited to the number of channels described above.

The biological information-transmitting portion 73 sequentially transmits the biological information acquired by the biological information-acquiring portion 72 to the real-time simultaneous measurement apparatus 8. The biological information-transmitting portion 73 may sequentially transmit the biological information to the multiple real-time simultaneous measurement apparatuses 8. In this case, the biological information-transmitting portion 73 sequentially transmits the biological information to the multiple real-time simultaneous measurement apparatuses 8, for example, by multicast. In a case where applications that operate on the multiple real-time simultaneous measurement apparatuses 8 use the biological information, they need only access their own shared memory, and delays in accessing a shared memory can be solved. The biological information-transmitting portion 73 is realized typically as a wireless or wired communication unit, but may be realized also as a broadcasting unit.

The real-time simultaneous measurement apparatus 8 is an apparatus that synchronizes and outputs the hemoglobin information and the brain wave information. Furthermore, it is preferable that the real-time simultaneous measurement apparatus 8 is an apparatus that synchronizes and outputs the hemoglobin information, the brain wave information, and the biological information.

In the information storage portion 80, information can be stored. Here, the information is an instruction to the test subject, information that is to be shown to the test subject to check reaction, or the like. The information storage portion 80 is preferably a non-volatile storage medium, but may be realized also as a volatile storage medium. There is no limitation on the procedure in which the information is stored in the information storage portion 80. For example, the information may be stored in the information storage portion 80 via a storage medium, the information transmitted via a communication line or the like may be stored in the information storage portion 80, or the information input via an input device may be stored in the information storage portion 80.

In the first shared memory 81, the hemoglobin information can be stored. In the second shared memory 82, the brain wave information can be stored. In the third shared memory 83, the biological information can be stored.

The first shared memory 81, the second shared memory 82, and the third shared memory 83 are typically realized as a non-volatile storage medium, but may be realized also as a volatile storage medium.

The information output portion 84 outputs the information stored in the information storage portion 80. Here, the output has a concept that includes display on a display screen, projection using a projector, printing in a printer, outputting a sound, transmission to an external apparatus, accumulation in a storage medium, delivery of a processing result to another processing apparatus or another program, and the like. The information output portion 84 may be considered to include or not to include an output device, such as a display screen or a loudspeaker. The information output portion 84 may be realized by as driver software for an output device, or a combination of driver software for an output device and the output device.

The hemoglobin information-receiving portion 85 sequentially receives the hemoglobin information from the NIRS brain-measuring apparatus 5. The hemoglobin information-receiving portion 85 is realized typically as a wireless or wired communication unit, but may be realized also as a unit that receives a broadcast.

The brain wave information-receiving portion 86 sequentially receives the brain wave information from the EEG brain wave-measuring apparatus 6. The brain wave information-receiving portion 86 is realized typically as a wireless or wired communication unit, but may be realized also as a unit that receives a broadcast.

The biological information-receiving portion 87 sequentially receives the biological information from the biological information-acquiring apparatus 7. The biological information-receiving portion 87 is realized typically as a wireless or wired communication unit, but may be realized also as a unit that receives a broadcast.

The synchronization processing portion 88 performs processing that synchronizes the hemoglobin information and the brain wave information. Furthermore, the synchronization processing portion 88 may perform processing that synchronizes the hemoglobin information, the brain wave information, and the biological information. Here, as described above, the biological information contains one or more types of information among electromyography information, electrooculography information, and electrocardiography information. The synchronization processing is, for example, processing that matches the numbers of information pieces of two or more types of information (e.g., the hemoglobin information and the brain wave information) sampled at different sampling frequencies. Furthermore, the synchronization processing is, for example, processing that matches the timings of starting information acquisition. The processing that matches the start timings is, for example, processing that deletes information before the start, thereby matching the information head positions of two or more types of information. In this case, start information is written in all of the hemoglobin information, the brain wave information, and the biological information. Furthermore, the synchronization processing is, for example, processing that checks a synchronization signal for two or more types of information, thereby matching the timings of the two or more types of information using the synchronization signal. Here, In this case, for example, the synchronization signal is written in all of the hemoglobin information, the brain wave information, and the biological information.

More specifically, the synchronization processing portion 88 synchronizes the hemoglobin information and the brain wave information, for example, by acquiring hemoglobin information or brain wave information corresponding to the larger sampling frequency, of the first sampling frequency and the second sampling frequency, without any processing on data, such as copying or thinning process, and subjecting brain wave information or hemoglobin information corresponding to the smaller sampling frequency to processing that copies information received at the closest time point so that the number of pieces of information is the same as that of the larger sampling frequency. In this case, the synchronization processing portion 88, for example, uses the start flag contained in the hemoglobin information and the brain wave information to align the first sampling data. Furthermore, the synchronization processing portion 88 may synchronize both types of data, by extrapolating or interpolating received information so that the number of pieces of brain wave information or hemoglobin information corresponding to the smaller sampling frequency is the same as that of the larger sampling frequency. Here, the extrapolating or interpolating processing is a known art, and, thus, a detailed description thereof has been omitted.

Furthermore, the synchronization processing portion 88 may synchronize the hemoglobin information and the brain wave information using another method. That is to say, for example, the synchronization processing portion 88 acquires hemoglobin information or brain wave information corresponding to the smaller sampling frequency, of the first sampling frequency and the second sampling frequency, without any processing on data as described above, and acquires brain wave information or hemoglobin information corresponding to the larger sampling frequency while thinning information so that the number of pieces of information is the same as that of the smaller sampling frequency. Also in this case, as described above, the synchronization processing portion 88, for example, uses the start flag contained in the hemoglobin information and the brain wave information to align the sampling data.

The synchronization processing portion 88 may be realized typically as an MPU, a memory, or the like. Typically, the processing procedure of the synchronization processing portion 88 is realized using software, and the software is stored in a storage medium, such as a ROM. Note that the processing procedure may be realized also using hardware (a dedicated circuit).

The synchronization processing unit 881 performs processing that synchronizes the received hemoglobin information and brain wave information. Furthermore, the synchronization processing unit 881 may perform processing that synchronizes the received hemoglobin information, brain wave information, and biological information. Examples of the synchronization processing are already shown. The synchronization processing unit 881 may be realized typically as an MPU, a memory, or the like. Typically, the processing procedure of the synchronization processing unit 881 is realized using software, and the software is stored in a storage medium, such as a ROM. Note that the processing procedure may be realized also using hardware (a dedicated circuit).

The hemoglobin information storing unit 882 stores the hemoglobin information processed by the synchronization processing unit 881 in the first shared memory 81.

The brain wave information storing unit 883 stores the brain wave information processed by the synchronization processing unit 881 in the second shared memory 82.

The biological information storing unit 884 stores the biological information processed by the synchronization processing unit 881 in the third shared memory 83. Here, each piece of information (the hemoglobin information, the brain wave information, and the biological information) processed by the synchronization processing unit 881 may be the same as each piece of received information.

The hemoglobin information storing unit 882, the brain wave information storing unit 883, and the biological information storing unit 884 may be realized typically as an MPU, a memory, or the like. Typically, the processing procedure of the hemoglobin information storing unit 882 and the like is realized using software, and the software is stored in a storage medium, such as a ROM. Note that the processing procedure may be realized also using hardware (a dedicated circuit).

The output portion 89 outputs the synchronized hemoglobin information and brain wave information. Furthermore, the output portion 89 may output the synchronized hemoglobin information, brain wave information, and biological information. Furthermore, it is preferable that the output portion 89 accumulates the synchronized hemoglobin information and brain wave information, and the information output by the information output portion 84 in association with each other. Moreover, it is preferable that the output portion 89 accumulates the synchronized hemoglobin information, brain wave information, and biological information, and the information output by the information output portion 84 in association with each other. Here, the output has a concept that includes display on a display screen, projection using a projector, printing in a printer, outputting a sound, transmission to an external apparatus, accumulation in a storage medium, delivery of a processing result to another processing apparatus or another program, and the like. Furthermore, the synchronized hemoglobin information and brain wave information, and the like can be used, for example, for presuming an intention of a handicapped person who cannot speak. Furthermore, the synchronized hemoglobin information and brain wave information, and the like can be used, for example, for presuming a brain state of the test subject. Furthermore, information in which the synchronized hemoglobin information and brain wave information, and the information output by the information output portion 84 are associated with each other can be used, for example, for determining and analyzing the relationship between the output information and the state of the brain waves of the test subject. Moreover, there is no limitation on the method for using the synchronized hemoglobin information and brain wave information, and the like. The output portion 89 may be considered to include or not to include an output device, such as a display screen or a loudspeaker. The output portion 89 may be realized by as driver software for an output device, or a combination of driver software for an output device and the output device.

Next, the operation of the real-time simultaneous measurement system will be described. Each of the NIRS brain-measuring apparatus 5, the EEG brain wave-measuring apparatus 6, and the biological information-acquiring apparatus 7 sequentially acquires corresponding information at a given sampling frequency according to the synchronization signal received from the synchronization signal output apparatus 4, and transmits the information to the real-time simultaneous measurement apparatus 8.

Next, the operation of the real-time simultaneous measurement apparatus 8 will be described with reference to the flowchart in FIG. 4.

(Step S401) The information output portion 84 judges whether or not it is time to output the information stored in the information storage portion 80. If it is time to output the information, the procedure proceeds to step S402. If it is not time to output the information, the procedure proceeds to step S404. Here, the information output portion 84 judges that it is time to output the information, for example, if an accepting unit (not shown) accepts an instruction from a user. Furthermore, the information output portion 84 may judge that it is time to output the information, for example, using, as a trigger, an event such as reaching a predetermined time.

(Step S402) The information output portion 84 acquires the information stored in the information storage portion 80. Here, the information output portion 84 acquires, for example, information corresponding to a user's instruction from the information storage portion 80.

(Step S403) The information output portion 84 outputs the information acquired in step S402. The procedure returns to step S401.

(Step S404) The hemoglobin information-receiving portion 85, the brain wave information-receiving portion 86, or the biological information-receiving portion 87 judges whether or not information has been received. If the information has been received, the procedure proceeds to step S405. If the information has not been received, the procedure proceeds to step S409.

(Step S405) The synchronization processing portion 88 performs synchronization processing. Examples of the synchronization processing will be described with reference to FIGS. 5 and 6.

(Step S406) The output portion 89 judges whether or not the synchronized information is present. If such information is present, the procedure proceeds to step S407. If such information is not present, the procedure returns to step S401.

(Step S407) The output portion 89 constructs information that is to be output. The output portion 89 constructs information that is to be output, for example, by associating the synchronized hemoglobin information and brain wave information, and the information output by the information output portion 84. Furthermore, the output portion 89 constructs information that is to be output, for example, by associating the synchronized hemoglobin information, brain wave information, and biological information, and the information output by the information output portion 84.

(Step S408) The output portion 89 outputs the information constructed in step S407. The procedure returns to step S401.

(Step S409) A unit (e.g., an accepting portion) (not shown) judges whether or not an end instruction has been accepted. If the end instruction has been accepted, the processing is ended. If the end instruction has not been accepted, the procedure returns to step S401.

Figure 4:
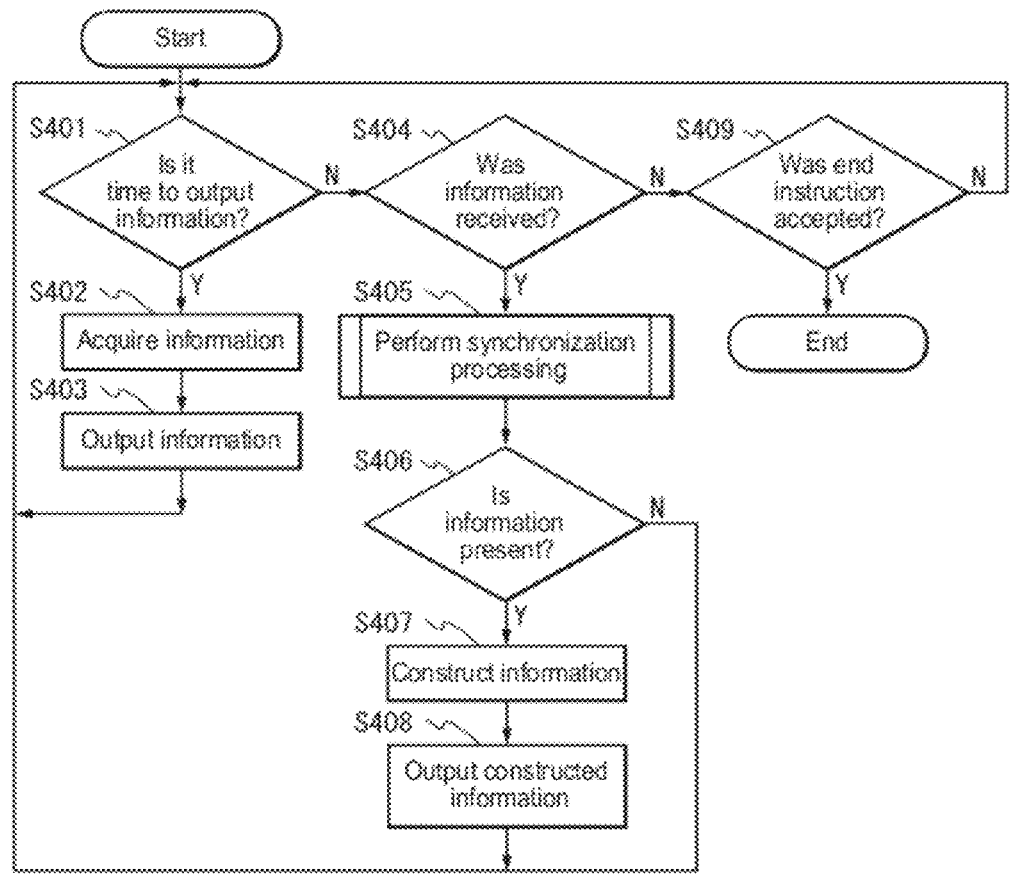
FIG. 4 is a flowchart illustrating the operation of the real-time simultaneous measurement apparatus in this embodiment.

Here, in the flowchart in FIG. 4, the real-time simultaneous measurement apparatus 8 may receive and process only the hemoglobin information and the brain wave information. In this case, the biological information-receiving portion 87 is not necessary.

Furthermore, in the flowchart in FIG. 4, the output portion 89 may construct information that is to be output, in which the information output by the information output portion 84 is not contained.

Next, a first example of the synchronization processing in step S405 will be described with reference to the flowchart in FIG. 5. The first synchronization processing is an example in which the synchronization processing is performed immediately after information is received.

(Step S501) The synchronization processing unit 881 judges whether or not there is a type of information that has not been received (one or two types of hemoglobin information, brain wave information, and biological information). If there is a type of information that has not been received, the procedure proceeds to step S502. If there is no such information, the procedure proceeds to step S503.

(Step S502) The synchronization processing unit 881 copies recently received information for the type of information that has not been received. With this copy processing, the number of pieces of information becomes the same in all types of information. That is to say, with the copy processing, the sampling frequency for acquiring information artificially becomes the same in all types of information.

(Step S503) The synchronization processing portion 88 (the hemoglobin information storing unit 882, the brain wave information storing unit 883, or the biological information storing unit 884) writes all types of information (the hemoglobin information and the brain wave information, or the hemoglobin information, the brain wave information, and the biological information) to different shared memories (the first shared memory 81, the second shared memory 82, or the third shared memory 83). The procedure returns to step S501. Here, the shared memory is a shared data-holding area on a memory or a file. Furthermore, the shared memory is a storage medium that is held by the real-time simultaneous measurement apparatus 8 and can be accessed by one or more applications or apparatuses (not shown).

Figure 5:
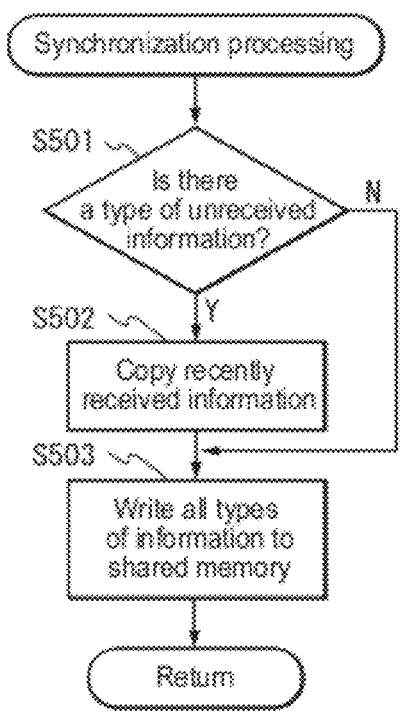
FIG. 5 is a flowchart illustrating an example of synchronization processing in this embodiment.

Here, in the flowchart in FIG. 5, the synchronization processing portion 88 writes information to the shared memory in step S503, but may perform another process on the information; for example, it may deliver the information to the output portion 89.

Figure 6:
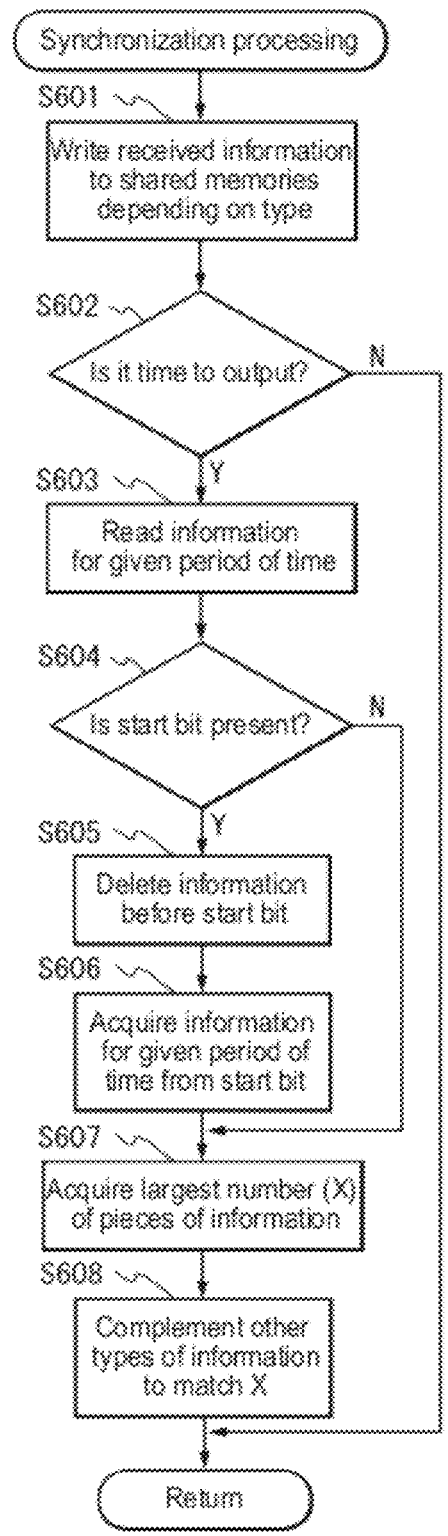
FIG. 6 is a flowchart illustrating an example of synchronization processing in this embodiment.

Next, a second example of the synchronization processing in step S405 will be described with reference to the flowchart in FIG. 6. The second synchronization processing is an example in which the synchronization processing is performed when information is output.

(Step S601) The synchronization processing portion 88 writes received information to different shared memories (the first shared memory 81, the second shared memory 82, or the third shared memory 83) depending on the type of information. Here, the type of information is, for example, hemoglobin information, brain wave information, or biological information.

(Step S602) The synchronization processing portion 88 judges whether or not it is time to output the information. If it is time to output the information, the procedure proceeds to step S603. If it is not time to output the information, the procedure returns to the upper-level processing. For example, the real-time simultaneous measurement apparatus 8 uses its own clock to judge whether or not it is time to output the information. For example, the real-time simultaneous measurement apparatus 8 outputs the information regularly (e.g., every 10 msec).

(Step S603) The synchronization processing portion 88 reads information for a given period of time from the current pointer for accessing information, from the shared memory. The synchronization processing portion 88 reads all types of information for each type of information and arranges the information in the memory. Here, if the information has been read, the pointer for accessing information moves to the next position for reading.

(Step S604) The synchronization processing portion 88 judges whether or not a start bit for synchronization is present in the information read in step S603. If the start bit is present, the procedure proceeds to step S605. If the start bit is not present, the procedure proceeds to step S607.

(Step S605) The synchronization processing portion 88 deletes information before the start bit in all types of information.

(Step S606) The synchronization processing portion 88 reads information for a given period of time from the start bit in all types of information, from the corresponding shared memory (the first shared memory 81, the second shared memory 82, or the third shared memory 83), and arranges the information in the memory.

(Step S607) The synchronization processing portion 88 acquires the largest number (X) of pieces of information among all types of information.

(Step S608) The synchronization processing portion 88 subjects a type of information that does not have the largest number of pieces of information to complementary processing so that the number of pieces of information is the same as the number (X) of pieces of information. The complementary processing is processing that copies recently received information or extrapolates or interpolates information so that the number of pieces of information is the same as the number (X) of pieces of information. The procedure returns to the upper-level processing.

Hereinafter, a specific operation of the real-time simultaneous measurement system in this embodiment will be described.

Figure 7:
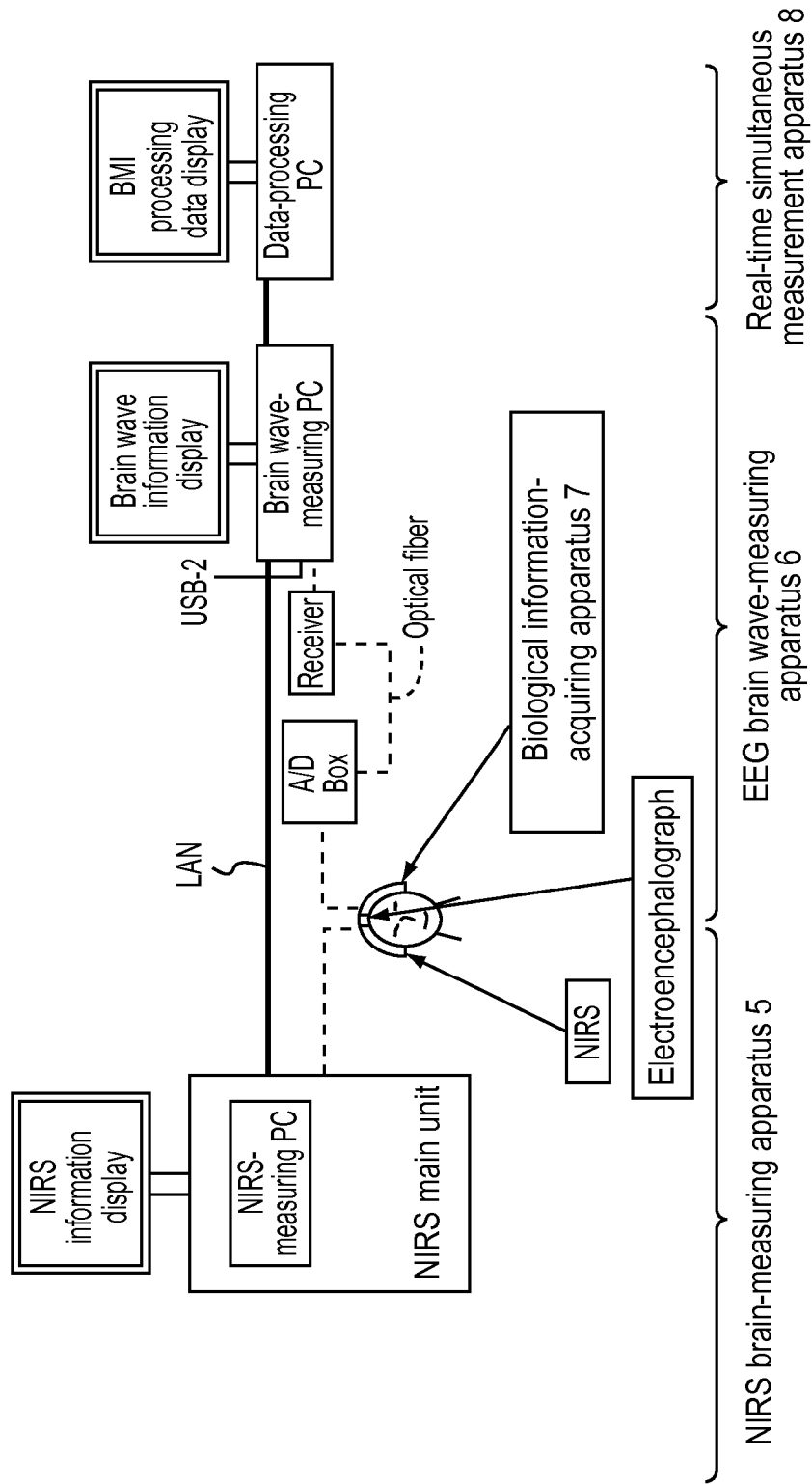
FIG. 7 is a view showing the installed real-time simultaneous measurement system in this embodiment.

FIG. 7 shows the installed real-time simultaneous measurement system. In FIG. 7, the synchronization signal output apparatus 4 is hidden. The synchronization signal output apparatus 4 is connected via a LAN and a BNC cable to the NIRS brain-measuring apparatus 5, the EEG brain wave-measuring apparatus 6, and the biological information-acquiring apparatus 7. Furthermore, in FIG. 7, BMI processing data refers to BMI (brain-machine interface) data (e.g., including the NIRS information, the brain wave information, the biological information, etc.) after synchronization.

Figure 8:
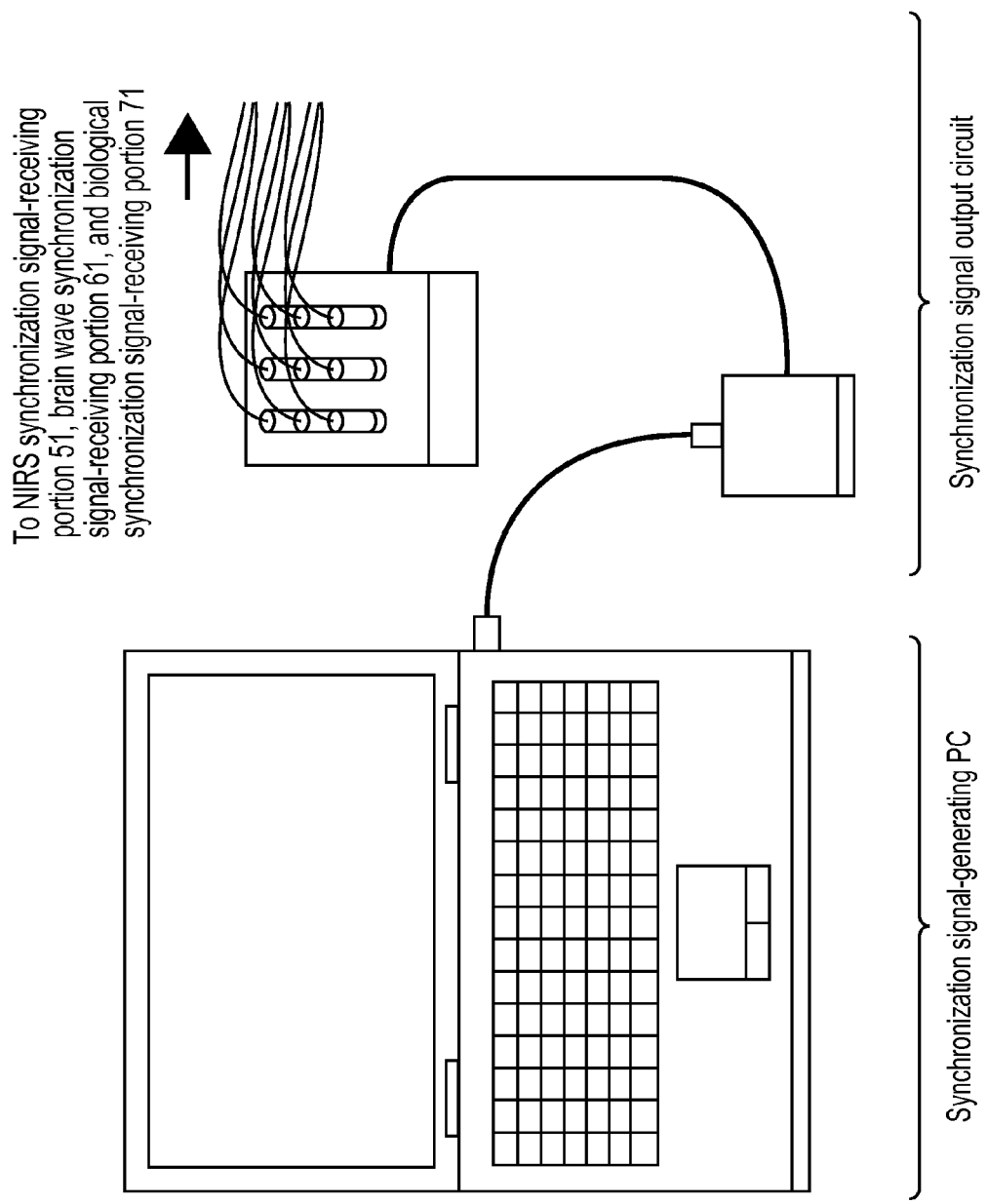
FIG. 8 is a view showing a synchronization signal output apparatus in this embodiment.

FIG. 8 shows the synchronization signal output apparatus 4. In FIG. 8, a PC for generating a synchronization signal generates a synchronization signal, and outputs the synchronization signal via a synchronization signal output circuit to the NIRS synchronization signal-receiving portion 51, the brain wave synchronization signal-receiving portion 61, and the biological synchronization signal-receiving portion 71.

Figure 9:
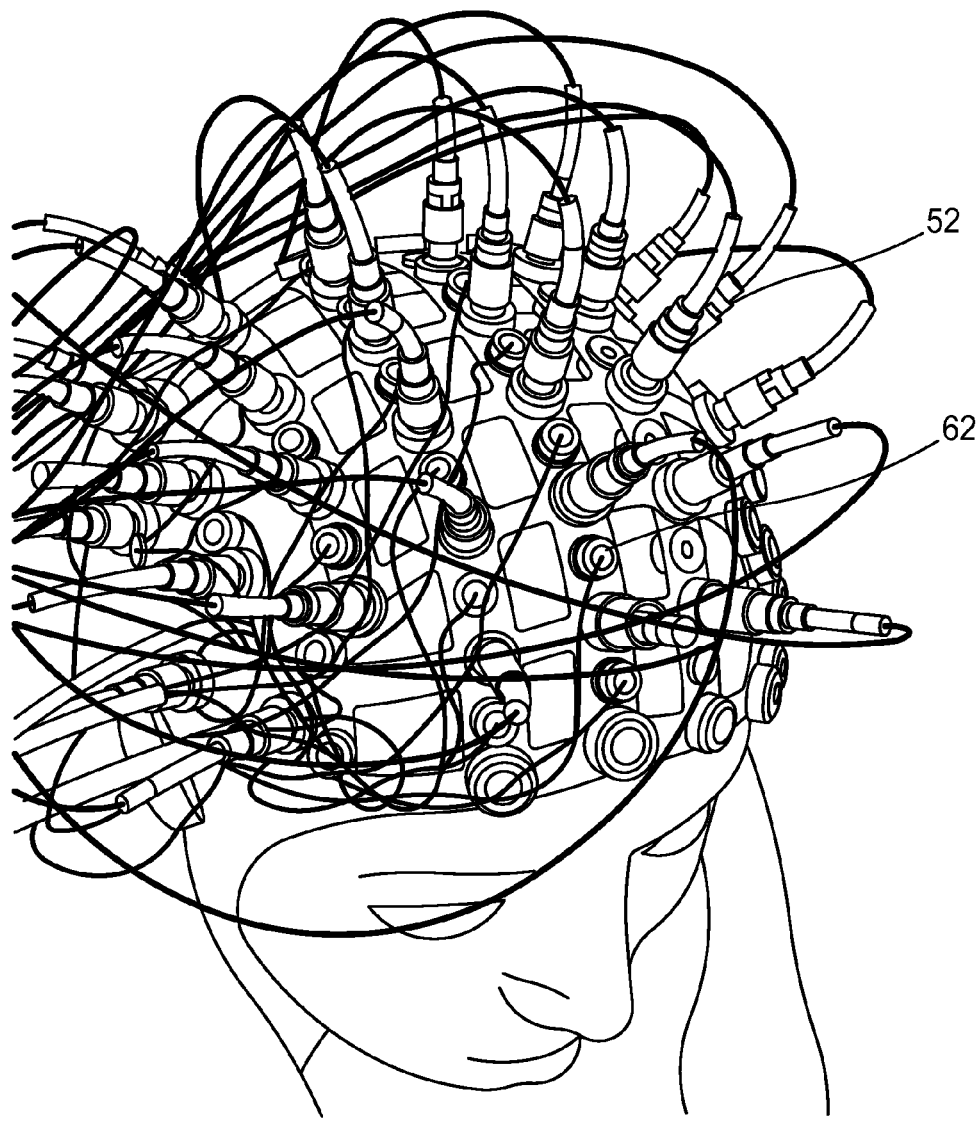
FIG. 9 is a view showing a measuring instrument that is worn on a head portion of a test subject in this embodiment.

FIG. 9 shows a measuring instrument that is worn on a head portion of a test subject. In FIG. 9, the hardware configuration of the hemoglobin information-acquiring portion 52 and the brain wave information-acquiring portion 62. Here, the hemoglobin information-acquiring portion 52 acquires hemoglobin information, which is the amount of hemoglobin, for example, by acquiring voltages obtained in the case where near infrared light having a wavelength of 780 nm, 805 nm, and 830 nm is generated and irradiated on a head portion and a voltage obtained in the case where no light is generated, and substituting the acquired voltages into a predetermined equation (an equation for calculating the amount of hemoglobin). Furthermore, the hemoglobin information-acquiring portion 52 acquires the hemoglobin information, for example, from 48 channels (the 48 measuring points that are present in FIG. 9). Here, the hemoglobin information-acquiring portion 52 holds information on the predetermined equation.

In this state, a user inputs an instruction to start measurement into the first operating apparatus 1. Then, the first instruction-accepting portion 11 accepts the instruction to start measurement. Next, the first instruction-transmitting portion 12 transmits the instruction to start measurement to the second operating apparatus 2 and the third operating apparatus 3. Then, the second instruction-receiving portion 21 of the second operating apparatus 2 and the third instruction-receiving portion 31 of the third operating apparatus 3 receive the instruction to start measurement. Next, the second instruction-transmitting portion 22 of the second operating apparatus 2 transmits the instruction to start measurement to the NIRS brain-measuring apparatus 5. Moreover, the third instruction-receiving portion 31 of the third operating apparatus 3 transmits the instruction to start measurement to the EEG brain wave-measuring apparatus 6. Here, the information transmitted to the NIRS brain-measuring apparatus 5 and the EEG brain wave-measuring apparatus 6 is, for example, the information shown in FIG. 10. FIG. 10 shows trigger information for giving a trigger to the NIRS brain-measuring apparatus 5, the EEG brain wave-measuring apparatus 6, the biological information-acquiring apparatus 7, and the like. The trigger information consists of, for example, 8 bits, and has a start bit (the 1st bit) indicating an instruction to start measurement, an end bit (the 2nd bit) indicating an instruction to end measurement, and an event bit (the 3rd bit) for synchronization. The 4th to 6th bits of the trigger information can be used, for example, for determining a task. Furthermore, the 7 and 8th bits can be used as a mark. The bit for determining a task is for saving data indicating information that was displayed by the information output portion 84. Furthermore, the mark is for saving data indicating a field or the like that the user wants to save during experiments.

Then, the NIRS synchronization signal-receiving portion 51 of the NIRS brain-measuring apparatus 5 receives the trigger information indicating the start. Next, the hemoglobin information-acquiring portion 52 sequentially acquires the hemoglobin information at a frequency (e.g., 40 Hz) specific to the NIRS brain-measuring apparatus 5. Then, the hemoglobin information-transmitting portion 53 sequentially transmits the hemoglobin information acquired by the hemoglobin information-acquiring portion 52 to the real-time simultaneous measurement apparatus 8.

Furthermore, the brain wave synchronization signal-receiving portion 61 of the EEG brain wave-measuring apparatus 6 receives the trigger information indicating the start. Next, the brain wave information-acquiring portion 62 sequentially acquires the brain wave information at a frequency (e.g., 1024 Hz) specific to the EEG brain wave-measuring apparatus 6. Then, the brain wave information-transmitting portion 63 sequentially transmits the brain wave information acquired by the brain wave information-acquiring portion 62 to the real-time simultaneous measurement apparatus 8.

Next, it is assumed that the information output portion 84 of the real-time simultaneous measurement apparatus 8 reads the information, "Raise your right hand." from the information storage portion 80, and displays the information on a display screen. Then, it is assumed that the test subject saw "Raise your right hand." displayed on the display screen, and raised his or her right hand. Here, still at this time point, the NIRS brain-measuring apparatus 5 continuously acquires and transmits the hemoglobin information, and the EEG brain wave-measuring apparatus 6 continuously acquires and transmits the brain wave information.

Next, the synchronization signal output apparatus 4 uses the first synchronization signal output unit 412 or the second synchronization signal output unit 413 according to the selection information stored in the selection information storage unit 411, to regularly (e.g., with a period of 1 kHz) transmit the synchronization signal to the NIRS brain-measuring apparatus 5 and the EEG brain wave-measuring apparatus 6. Here, for example, the synchronization signal transmitted by the second synchronization signal output unit 413 has a structure similar to that of the trigger information in FIG. 10, and is information in which the 3rd bit is "1" and the other bits are "0".

Then, the NIRS synchronization signal-receiving portion 51 of the NIRS brain-measuring apparatus 5 and the brain wave synchronization signal-receiving portion 61 of the EEG brain wave-measuring apparatus 6 receive trigger information, which is a synchronization signal. Then, according to the synchronization signal, the hemoglobin information-acquiring portion 52 of the NIRS brain-measuring apparatus 5 acquires the hemoglobin information, and the hemoglobin information-transmitting portion 53 transmits the hemoglobin information to the real-time simultaneous measurement apparatus 8. Furthermore, according to the synchronization signal, the brain wave information-acquiring portion 62 of the EEG brain wave-measuring apparatus 6 acquires the brain wave information, and the brain wave information-transmitting portion 63 transmits the brain wave information to the real-time simultaneous measurement apparatus 8.

Figure 13:
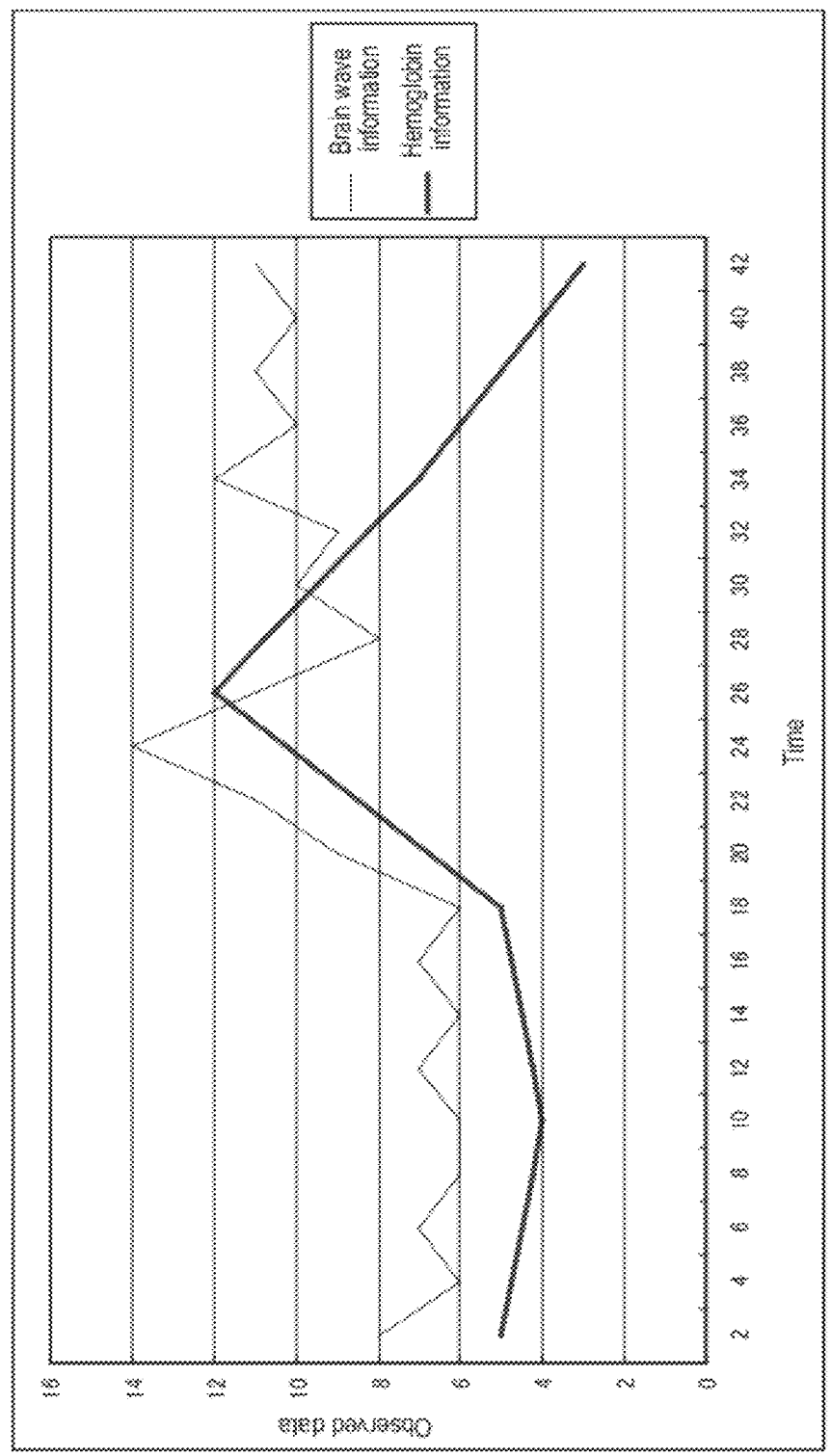
FIG. 13 is a graph showing information received by the real-time simultaneous measurement apparatus in this embodiment.

Then, the real-time simultaneous measurement apparatus 8, for example, sequentially receives the hemoglobin information shown FIG. 11 from the NIRS brain-measuring apparatus 5. Furthermore, the real-time simultaneous measurement apparatus 8, for example, sequentially receives the brain wave information shown in FIG. 12 from the EEG brain wave-measuring apparatus 6. Here, in FIG. 11, the hemoglobin information is received every 8 msec. In FIG. 12, the brain wave information is received every 2 msec. From FIGS. 11 and 12, it is seen that the first sampling frequency for acquiring the hemoglobin information in the NIRS brain-measuring apparatus 5 and the second sampling frequency for acquiring the brain wave information in the EEG brain wave-measuring apparatus 6 differ. The first sampling frequency and the second sampling frequency are in a ratio of 1:4 in this example. Here, FIG. 13 is a graph showing the information in FIGS. 11 and 12.

Next, the synchronization processing portion 88 performs the following synchronization processing, for example, every 2 msec. That is to say, if both the brain wave information and the hemoglobin information are received, the synchronization processing portion 88 writes both types of information to the first shared memory 81 or the second shared memory 82. Furthermore, if only the brain wave information is received, the synchronization processing portion 88 writes the brain wave information to the second shared memory 82, and complements the hemoglobin information. This sort of complement is performed, for example, by writing recently received hemoglobin information to the first shared memory 81. With this processing, the synchronization processing portion 88 obtains the synchronized brain wave information and hemoglobin information. That is to say, the synchronization processing portion 88 obtains the brain wave information and the hemoglobin information as shown in the graph in FIG. 14.

Figure 14:
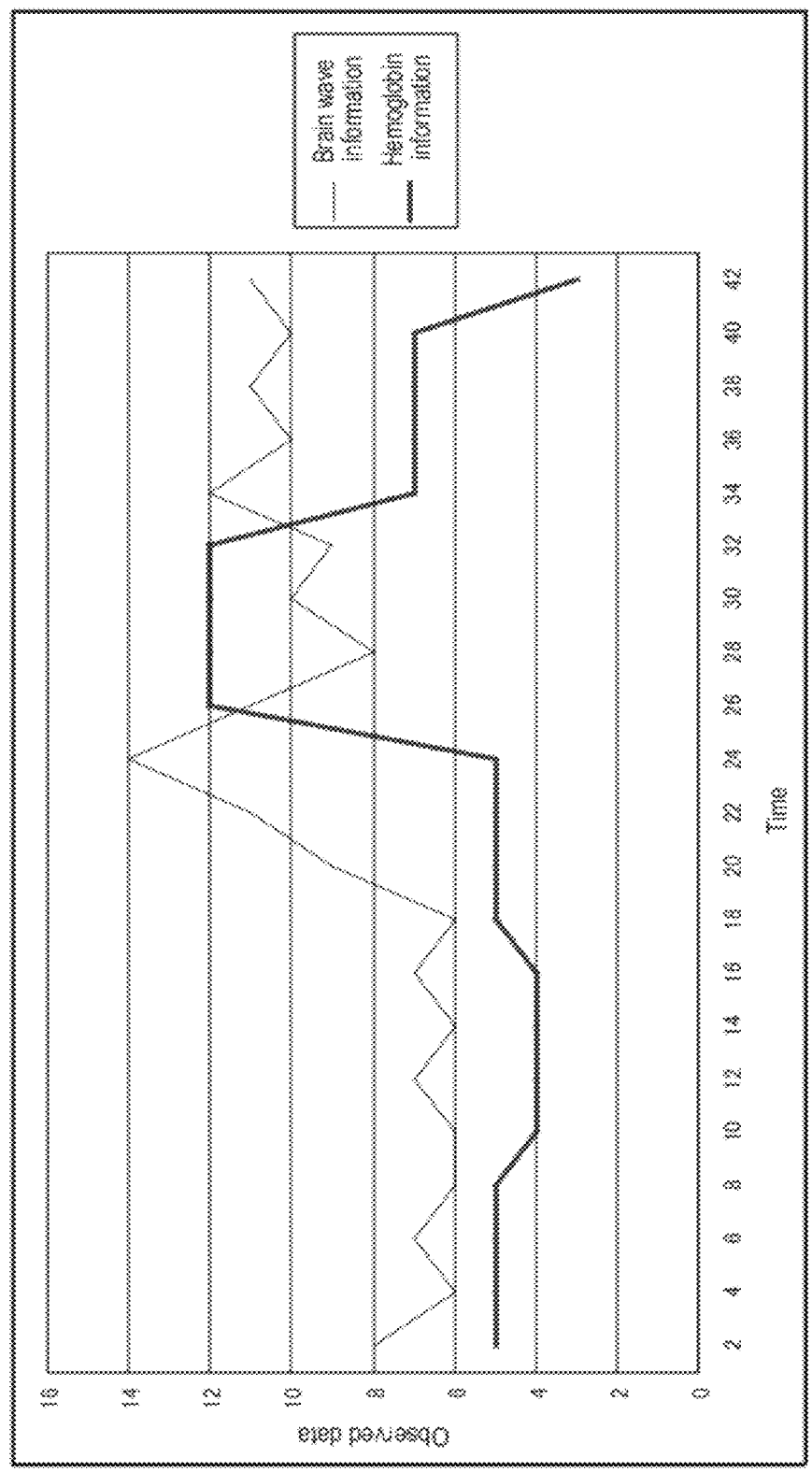
FIG. 14 is a graph after synchronization processing in this embodiment.

Next, the output portion 89 outputs the synchronized brain wave information and hemoglobin information. FIG. 14 shows an example of the output. Here, the output portion 89 may deliver the information in FIG. 15, for example, to another processing apparatus or another program. The information in FIG. 15 is information from which the graph in FIG. 14 is constructed.

Here, in FIGS. 11 and 12 and the like, both types of the hemoglobin information and the brain wave information are information acquired from one channel. However, the hemoglobin information and the brain wave information are typically acquired from two or more channels.

Furthermore, in the foregoing specific example, the synchronization processing portion 88 performs processing that synchronizes the hemoglobin information and the brain wave information. However, it is preferable that the synchronization processing portion 88 performs processing that synchronizes the hemoglobin information, the brain wave information, and the biological information using the same algorithm.

As described above, according to this embodiment, the NIRS data obtained by measuring a change in blood flow derived from brain activity and the EEG data obtained by measuring electrical activity derived from brain activity can be simultaneously and synchronously acquired and used in real time. Thus, the brain state can be precisely determined, and the relationship between a change in blood flow and electrical activity derived from brain activity, which cannot be checked with existing techniques, can be checked.

Furthermore, according to this embodiment, the hemoglobin information, the brain wave information, and the biological information can be simultaneously and synchronously acquired and used in real time. Thus, the brain state can be more precisely determined, and the relationship between a change in blood flow and electrical activity derived from brain activity, which cannot be checked with existing techniques, can be checked.

Furthermore, according to this embodiment, a synchronization signal is transmitted from the synchronization signal output apparatus 4 to the NIRS brain-measuring apparatus 5 and the EEG brain wave-measuring apparatus 6, or to the NIRS brain-measuring apparatus 5, the EEG brain wave-measuring apparatus 6, and the biological information-acquiring apparatus 7, and information is synchronously acquired. Thus, the information can be precisely synchronized, and the brain state can be more precisely determined. That is to say, measurement of brain activity requires a precision of several tens of msec, and, thus, the synchronization signal from the synchronization signal output apparatus 4 is important to satisfy this requirement. If the synchronization signal output apparatus 4 is not present, the time for the NIRS brain-measuring apparatus 5 and the EEG brain wave-measuring apparatus 6 to start measurement or store information may be shifted by several hundreds of msec to several seconds.

More specifically, this real-time simultaneous measurement system can be used, for example, for rehabilitation, because the system enables the hemoglobin information and the brain wave information to be simultaneously and synchronously acquired and used in real time. That is to say, even in the case where a patient whose brain was partially injured is trying unsuccessfully to move his or her arm or foot, this information-processing system shows the patient that their brain activity is normal or no longer abnormal, and, thus, motivation in rehabilitation can be maintained.

Furthermore, this real-time simultaneous measurement system can be used, for example, for image training in sports. That is to say, whether or not brain activity is in an image training state during user image training can be seen, and, thus, this system can contribute to appropriate image training.

Moreover, this real-time simultaneous measurement system can be used, for example, for training the user to control the user's feelings. That is to say, the fact that the user's feelings are excited is seen in real time, and, thus, training to suppress feelings of excitement becomes possible.

Here, in this embodiment, there is no limitation on the algorithm or timing for synchronization. That is to say, for example, the NIRS brain-measuring apparatus 5, the EEG brain wave-measuring apparatus 6, and the biological information-acquiring apparatus 7 respectively acquire and store the hemoglobin information, the brain wave information, and the biological information. The hemoglobin information, the brain wave information, and the biological information are paired with synchronization signals (e.g., time information). Next, the NIRS brain-measuring apparatus 5, the EEG brain wave-measuring apparatus 6, and the biological information-acquiring apparatus 7 transmit the hemoglobin information, the brain wave information, and the biological information without matching the timings (at any timing) to the real-time simultaneous measurement apparatus 8. Then, the real-time simultaneous measurement apparatus 8 synchronizes the hemoglobin information, the brain wave information, and the biological information using the synchronization signals, through processing similar to that described above. Here, the real-time simultaneous measurement apparatus 8 may perform processing that synchronizes only two types of information freely selected from the hemoglobin information, the brain wave information, and the biological information. Here, it will be appreciated that the synchronization signal may be information other than the time information as long as it is information that can be used for synchronization.

Furthermore, according to this embodiment, various modes in which the synchronized hemoglobin information and brain wave information, and the like are used are possible, and there is no limitation on the usage mode.

Furthermore, in this embodiment, the real-time simultaneous measurement system may acquire multiple pieces of hemoglobin information by using multiple NIRS brain-measuring apparatuses 5 in a coupled state.

Figure 16:
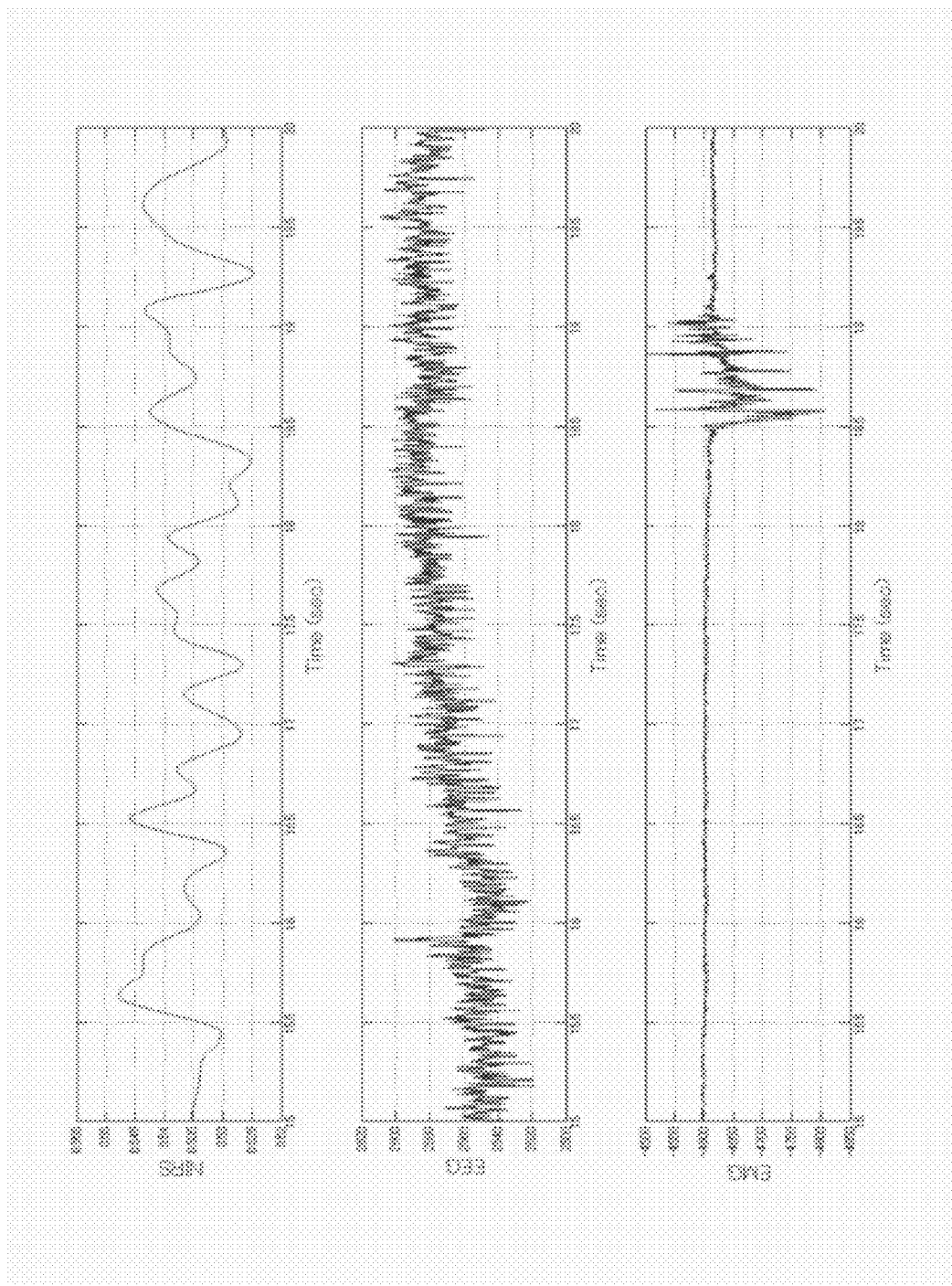
FIG. 16 shows exemplary graphs after synchronization processing in this embodiment.

Furthermore, in the foregoing specific example of this embodiment, the hemoglobin information and the brain wave information are simultaneously and synchronously acquired and output in real time. However, with the real-time simultaneous measurement system, the hemoglobin information (NIRS), the brain wave information, and the biological information (e.g., EMG) may be simultaneously and synchronously acquired and output in real time. FIG. 16 shows an example of the output in this case.

Figure 17:
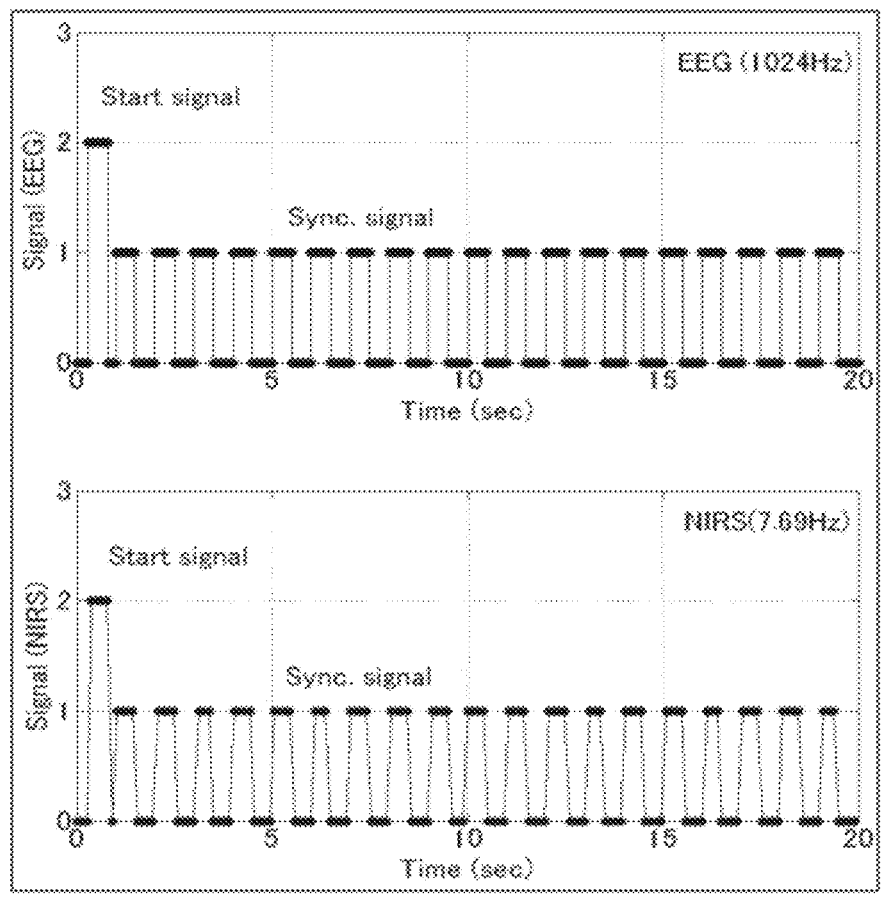
FIG. 17 shows exemplary graphs of synchronization signals received by a brain wave synchronization signal-receiving portion and a NIRS synchronization signal-receiving portion in this embodiment.

FIG. 17 shows an example in which synchronization signals output by the synchronization signal output apparatus 4 are received by the brain wave synchronization signal-receiving portion 61 and the NIRS synchronization signal-receiving portion 51 in the foregoing specific example of this embodiment. In the example in FIG. 17, the sampling frequency of the brain wave synchronization signal-receiving portion 61 is 1024 Hz, the sampling frequency of the NIRS synchronization signal-receiving portion 51 is 7.69 Hz, the signal "2" is output as a start signal, and the signal "1" is output as a synchronization signal.

The processing in this embodiment may be realized using software. The software may be distributed by software download or the like. The software may be distributed in a form where the software is stored in a storage medium, such as a CD-ROM. Furthermore, this software may be distributed as a computer program product. Note that the same is applied to other embodiments described in this specification. The software that realizes the real-time simultaneous measurement apparatus in this embodiment may be the following program. Specifically, this program is a program for causing a computer to function as: a hemoglobin information-receiving portion that sequentially receives hemoglobin information, which is information relating to the amount of hemoglobin in a head portion of a test subject, from a NIRS brain-measuring apparatus that receives a synchronization signal output by a synchronization signal output apparatus and acquires the hemoglobin information when the synchronization signal has been received; a brain wave information-receiving portion that sequentially receives brain wave information, which is information relating to the brain waves of the test subject, from an EEG brain wave-measuring apparatus that receives a synchronization signal output by the synchronization signal output apparatus and acquires the brain wave information when the synchronization signal has been received; a synchronization processing portion that performs processing that synchronizes the hemoglobin information and the brain wave information; and an output portion that outputs the synchronized hemoglobin information and brain wave information.

Furthermore, in this program, it is preferable that the synchronization signal output portion comprises: a first synchronization signal output unit that outputs a synchronization signal realized by an electrical signal to the NIRS brain-measuring apparatus and the EEG brain wave-measuring apparatus; a second synchronization signal output unit that outputs a synchronization signal realized using software to the NIRS brain-measuring apparatus and the EEG brain wave-measuring apparatus; a selection information storage unit in which selection information indicating which synchronization signal output unit, of the first and second synchronization signal output units, outputs a synchronization signal is stored; and a synchronization signal output-instructing unit that gives either the first synchronization signal output unit or the second synchronization signal output unit an instruction to output a synchronization signal, according to the selection information.

Furthermore, in this program, it is preferable that the synchronization processing portion comprises: a synchronization processing unit that performs processing that synchronizes the hemoglobin information and the brain wave information; a hemoglobin information storing unit that writes the hemoglobin information processed by the synchronization processing unit to the first shared memory; and a brain wave information storing unit that writes the brain wave information processed by the synchronization processing unit to the second shared memory.

Furthermore, in this program, it is preferable that the computer is caused to further function as an information output portion that outputs information stored in a storage medium, wherein the output portion accumulates the synchronized hemoglobin information and brain wave information, and the information output by the information output portion in association with each other.

Furthermore, in this program, it is preferable that a first sampling frequency at which the hemoglobin information-acquiring portion acquires the hemoglobin information and a second sampling frequency at which the brain wave information-acquiring portion acquires the brain wave information differ, and the synchronization processing portion synchronizes the hemoglobin information and the brain wave information by acquiring hemoglobin information or brain wave information corresponding to the larger sampling frequency, of the first sampling frequency and the second sampling frequency, and subjecting brain wave information or hemoglobin information corresponding to the smaller sampling frequency to processing that copies information received at the closest time point or processing that extrapolates or interpolates received information so that the number of pieces of information is the same as that of the larger sampling frequency.

Furthermore, in this program, it is preferable that the computer is caused to further function as a biological information-receiving portion that sequentially receives biological information, the synchronization processing portion of the real-time simultaneous measurement apparatus performs processing that synchronizes the hemoglobin information, the brain wave information, and the biological information, and the output portion outputs the synchronized hemoglobin information, brain wave information, and biological information.

Figure 18:
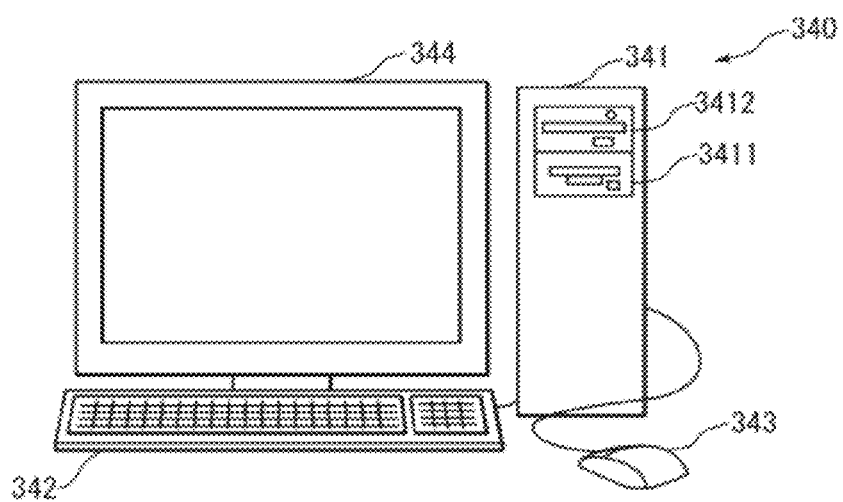
FIG. 18 is a schematic view of a computer system that realizes the real-time simultaneous measurement apparatus and the like in this embodiment.
Figure 19:
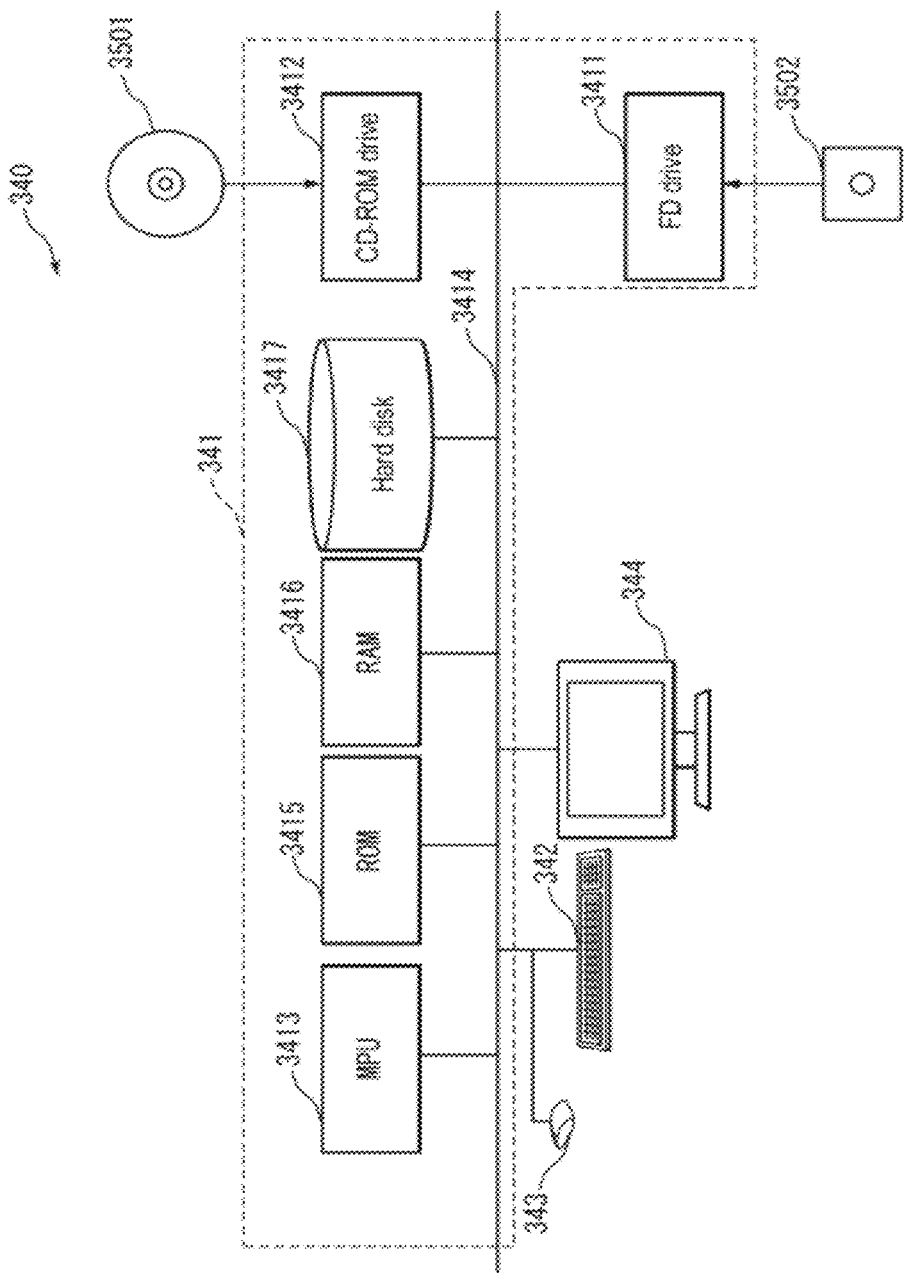
FIG. 19 is a diagram showing the internal configuration of a computer system in this embodiment.

FIG. 18 shows the external appearance of a computer that executes the programs described in this specification to realize the real-time simultaneous measurement apparatus and the like in the foregoing embodiments. The foregoing embodiments may be realized using computer hardware and a computer program executed thereon. FIG. 18 is a schematic view of a computer system 340. FIG. 19 is a diagram showing the internal configuration of the computer system 340.

In FIG. 18, the computer system 340 includes a computer 341 including an FD drive 3411 and a CD-ROM drive 3412, a keyboard 342, a mouse 343, and a monitor 344.

In FIG. 19, the computer 341 includes not only the FD drive 3411 and the CD-ROM drive 3412, but also an MPU 3413, a bus 3414 that is connected to the CD-ROM drive 3412 and the FD drive 3411, a ROM 3415 in which a program such as a startup program is to be stored, a RAM 3416 that is connected to the CPU 3413 and in which a command of an application program is temporarily stored and a temporary storage area is to be provided, and a hard disk 3417 in which an application program, a system program, and data are to be stored. Although not shown, the computer 341 may further include a network card that provides connection to a LAN.

The program for causing the computer system 340 to execute the functions of the real-time simultaneous measurement apparatus and the like in the foregoing embodiments may be stored in a CD-ROM 3501 or an FD 3502, inserted into the CD-ROM drive 3412 or the FD drive 3411, and transmitted to the hard disk 3417. Alternatively, the program may be transmitted via a network (not shown) to the computer 341 and stored in the hard disk 3417. At the time of execution, the program is loaded into the RAM 3416. The program may be loaded from the CD-ROM 3501 or the FD 3502, or directly from a network.

The program does not necessarily have to include, for example, an operating system (OS) or a third party program to cause the computer 341 to execute the functions of the real-time simultaneous measurement apparatus and the like in the foregoing embodiments. The program may only include a command portion to call an appropriate function (module) in a controlled mode and obtain the desired results. The manner in which the computer system 340 operates is well known, and, thus, a detailed description thereof has been omitted.

It should be noted that, in the program, in a transmitting step of transmitting information, a receiving step of receiving information, or the like, the processing that is performed by hardware, for example, processing performed by a modem or an interface card in the transmitting step (processing that can be performed only by such hardware) is not included.

Furthermore, the computer that executes this program may be a single computer, or may be multiple computers. More specifically, centralized processing may be performed, or distributed processing may be performed.

Furthermore, in the foregoing embodiments, it will be appreciated that two or more communication units (an instruction-accepting portion, an instruction-transmitting portion, etc.) in one apparatus may be physically realized as one medium.

Furthermore, in the foregoing embodiments, each process (each function) may be realized as integrated processing using a single apparatus (system), or may be realized as distributed processing using multiple apparatuses.

The present invention is not limited to the embodiments set forth herein. Various modifications are possible within the scope of the present invention.

As described above, the real-time simultaneous measurement system according to the present invention has an effect that can precisely synchronize the NIRS measurement information and the EEG measurement information, and, thus, this system is useful, for example, as a real-time simultaneous measurement system and the like.

What is claimed is:

1. A real-time simultaneous measurement system, comprising
    a synchronization signal output apparatus,
    a NIRS brain-measuring apparatus,
    an EEG brain wave-measuring apparatus, and
    a real-time simultaneous measurement apparatus,
    wherein the synchronization signal output apparatus comprises:
        a synchronization signal output portion that outputs a synchronization signal, which is a signal for synchronizing acquisition of information in the NIRS brain-measuring apparatus and the EEG brain wave-measuring apparatus, to the NIRS brain-measuring apparatus and the EEG brain wave-measuring apparatus;
    the NIRS brain-measuring apparatus comprises:
        a NIRS synchronization signal-receiving portion that receives the synchronization signal from the synchronization signal output apparatus;
        a hemoglobin information-acquiring portion that acquires hemoglobin information, which is information relating to an amount of hemoglobin in a head portion of a test subject, when the synchronization signal has been received by the NIRS synchronization signal-receiving portion; and
        a hemoglobin information-transmitting portion that sequentially transmits the hemoglobin information to the real-time simultaneous measurement apparatus;
    the EEG brain wave-measuring apparatus comprises:
        a brain wave synchronization signal-receiving portion that receives the synchronization signal from the synchronization signal output apparatus;
        a brain wave information-acquiring portion that acquires brain wave information, which is information relating to brain waves of the test subject, when the synchronization signal has been received by the brain wave synchronization signal-receiving portion; and
        a brain wave information-transmitting portion that sequentially transmits the brain wave information to the real-time simultaneous measurement apparatus; and
    the real-time simultaneous measurement apparatus comprises:
        a hemoglobin information-receiving portion that sequentially receives the hemoglobin information;
        a brain wave information-receiving portion that sequentially receives the brain wave information;
        a synchronization processing portion that performs processing that synchronizes the hemoglobin information and the brain wave information; and
        an output portion that outputs the synchronized hemoglobin information and brain wave information, and wherein the synchronization signal output portion of the synchronization signal output apparatus comprises:
- a first synchronization signal output unit that outputs a synchronization signal realized by an electrical signal to the NIRS brain-measuring apparatus and the EEG brain wave-measuring apparatus;
- a second synchronization signal output unit that outputs a synchronization signal realized using software to the NIRS brain-measuring apparatus and the EEG brain wave-measuring apparatus;
- a selection information storage unit in which selection information indicating which synchronization signal output unit, of the first and second synchronization signal output units, outputs a synchronization signal is stored; and
- a synchronization signal output-instructing unit that gives either the first synchronization signal output unit or the second synchronization signal output unit an instruction to output a synchronization signal, according to the selection information.

2. The real-time simultaneous measurement system according to claim 1,
wherein the real-time simultaneous measurement apparatus further comprises:
- a first shared memory in which the hemoglobin information can be stored; and
- a second shared memory in which the brain wave information can be stored; and
the synchronization processing portion comprises:
- a synchronization processing unit that performs processing that synchronizes the hemoglobin information and the brain wave information;
- a hemoglobin information storing unit that writes the hemoglobin information processed by the synchronization processing unit to the first shared memory; and
- a brain wave information storing unit that writes the brain wave information processed by the synchronization processing unit to the second shared memory.

3. The real-time simultaneous measurement system according to claim 1, further comprising:
a first operating apparatus,
a second operating apparatus, and
a third operating apparatus,
wherein the first operating apparatus comprises:
- a first instruction-accepting portion that accepts an instruction from a user; and
- a first instruction-transmitting portion that transmits the instruction to the second operating apparatus and the third operating apparatus;
the second operating apparatus comprises:
- a second instruction-receiving portion that receives the instruction from the first operating apparatus; and
- a second instruction-transmitting portion that transmits the instruction received by the second instruction-receiving portion to the NIRS brain-measuring apparatus; and
the third operating apparatus comprises:
- a third instruction-receiving portion that receives the instruction from the first operating apparatus; and
- a third instruction transmitting portion that transmits the instruction received by the third instruction-receiving portion to the EEG brain wave-measuring apparatus.

4. The real-time simultaneous measurement system according to claim 1,
wherein the real-time simultaneous measurement apparatus further comprises:
- an information storage portion in which information can be stored; and
- an information output portion that outputs the information; and
the output portion accumulates the synchronized hemoglobin information and brain wave information, and the information output by the information output portion in association with each other in the information storage portion.

5. The real-time simultaneous measurement system according to claim 1,
wherein a first sampling frequency at which the hemoglobin information-acquiring portion acquires the hemoglobin information and a second sampling frequency at which the brain wave information-acquiring portion acquires the brain wave information differ, and
the synchronization processing portion synchronizes the hemoglobin information and the brain wave information by acquiring hemoglobin information or brain wave information corresponding to the larger sampling frequency, of the first sampling frequency and the second sampling frequency, and subjecting brain wave information or hemoglobin information corresponding to the smaller sampling frequency to processing that copies information received at the closest time point or processing that extrapolates or interpolates received information so that the number of pieces of information is the same as that of the larger sampling frequency.

6. The real-time simultaneous measurement system according to claim 1,
wherein the real-time simultaneous measurement system further comprises a biological information-acquiring apparatus,
the biological information-acquiring apparatus comprises:
- a biological information-acquiring portion that sequentially acquires biological information, which is information relating to a living body, from at least one section of the test subject; and
- a biological information-transmitting portion that sequentially transmits the biological information to the real-time simultaneous measurement apparatus;
the real-time simultaneous measurement apparatus further comprises a biological information-receiving portion that sequentially receives the biological information,
the synchronization processing portion of the real-time simultaneous measurement apparatus performs processing that synchronizes the hemoglobin information, the brain wave information, and the biological information, and
the output portion outputs the synchronized hemoglobin information, brain wave information, and biological information.

7. The real-time simultaneous measurement system according to claim 6, wherein the biological information-acquiring portion sequentially acquires electromyography information, which is information relating to electromyography, from the whole or part of the body of the test subject, electrooculography information, which is information relating to electrooculography, from sections surrounding the eyes of the test subject, or electrocardiography information, which is information relating to electrocardiography, from sections surrounding the heart of the test subject.

8. The real-time simultaneous measurement system according to claim 1, wherein each of the hemoglobin information and the brain wave information has a synchronization signal associated therewith, the real-time simultaneous measurement apparatus receives the hemoglobin information associated with the synchronization signal and the brain wave information associated with the synchronization signal at different timings, and the synchronization processing portion receives the hemoglobin information associated with the synchronization signal and the brain wave information associated with the synchronization signal, and then performs processing that synchronizes the hemoglobin information and the brain wave information.

9. The real-time simultaneous measurement system according to claim 6, wherein each of the hemoglobin information, the brain wave information, and the biological information has a synchronization signal associated therewith, the real-time simultaneous measurement apparatus receives the hemoglobin information associated with the synchronization signal, the brain wave information associated with the synchronization signal, and the biological information associated with the synchronization signal at different timings, and the synchronization processing portion receives the hemoglobin information associated with the synchronization signal, the brain wave information associated with the synchronization signal, and the biological information associated with the synchronization signal, and then performs processing that synchronizes the hemoglobin information, the brain wave information, and the biological information.

10. The real-time simultaneous measurement system according to claim 1, comprising a synchronization signal output apparatus, a NIRS brain-measuring apparatus, an EEG brain wave-measuring apparatus, and multiple real-time simultaneous measurement apparatuses, wherein the hemoglobin information-transmitting portion and the brain wave information-transmitting portion respectively transmit the hemoglobin information and the brain wave information to the multiple real-time simultaneous measurement apparatuses.

11. The real-time simultaneous measurement system according to claim 6, comprising a synchronization signal output apparatus, a NIRS brain-measuring apparatus, an EEG brain wave-measuring apparatus, a biological information-acquiring apparatus, and multiple real-time simultaneous measurement apparatuses, wherein the hemoglobin information-transmitting portion, the brain wave information-transmitting portion, and the biological information-transmitting portion respectively transmit the hemoglobin information, the brain wave information, and the biological information to the multiple real-time simultaneous measurement apparatuses.

12. A real-time simultaneous measurement method realized using a hemoglobin information-receiving portion, a brain wave information-receiving portion, a synchronization processing portion, and an output portion, comprising:

a hemoglobin information-receiving step, using the hemoglobin information-receiving portion, of sequentially receiving hemoglobin information, which is information relating to an amount of hemoglobin in a head portion of a test subject, from a NIRS brain-measuring apparatus that receives a synchronization signal output by a synchronization signal output portion of a synchronization signal output apparatus and acquires the hemoglobin information when the synchronization signal has been received, wherein the synchronization signal output apparatus outputs a first synchronization signal realized by an electrical signal to the NIRS brain-measuring apparatus and an EEG brain wave-measuring apparatus;

outputs a second synchronization signal realized using software to the NIRS brain-measuring apparatus and the EEG brain wave-measuring apparatus; and outputs either the first synchronization signal or the second synchronization signal, according to a selection information which is stored in a selection information storage unit and which indicates which synchronization signal of the first and second synchronization signals is output;

a brain wave information-receiving step, using the brain wave information-receiving portion, of sequentially receiving brain wave information, which is information relating to brain waves of the test subject, from the EEG brain wave-measuring apparatus that receives the synchronization signal output by the synchronization signal output apparatus and acquires the brain wave information when the synchronization signal has been received;

a synchronization processing step, using the synchronization processing portion, of performing processing that synchronizes the hemoglobin information and the brain wave information; and an output step, using the output portion, of outputting the synchronized hemoglobin information and brain wave information.

13. A non-transitory storage medium in which a program is stored, the program causing a computer to execute:

a hemoglobin information-receiving step of sequentially receiving hemoglobin information, which is information relating to an amount of hemoglobin in a head portion of a test subject, from a NIRS brain-measuring apparatus that receives a synchronization signal output by a synchronization signal output portion of a synchronization signal output apparatus and acquires the hemoglobin information when the synchronization signal has been received, wherein the synchronization signal output apparatus outputs a first synchronization signal realized by an electrical signal to the NIRS brain-measuring apparatus and an EEG brain wave-measuring apparatus;

outputs a second synchronization signal realized using software to the NIRS brain-measuring apparatus and the EEG brain wave-measuring apparatus; and outputs either the first synchronization signal or the second synchronization signal, according to a selection information which is stored in a selection information storage unit and which indicates which synchronization signal of the first and second synchronization signals is output;

a brain wave information-receiving step of sequentially receiving brain wave information, which is information relating to brain waves of the test subject, from the EEG brain wave-measuring apparatus that receives the synchronization signal output by the synchronization signal output apparatus and acquires the brain wave information when the synchronization signal has been received;

a synchronization processing step of performing processing that synchronizes the hemoglobin information and the brain wave information; and an output step of outputting the synchronized hemoglobin information and brain wave information.

* * * * *